US008882851B2

(12) United States Patent
Smith

(10) Patent No.: US 8,882,851 B2
(45) Date of Patent: Nov. 11, 2014

(54) IMPLANTABLE PROSTHETIC DEVICE FOR DISTRIBUTION OF WEIGHT ON AMPUTATED LIMB AND METHOD OF USE WITH AN EXTERNAL PROSTHETIC DEVICE

(76) Inventor: Larry Nelson Smith, Gainesville, FL (US)

( * ) Notice: Subject to any disclaimer, the term of this patent is extended or adjusted under 35 U.S.C. 154(b) by 153 days.

(21) Appl. No.: 13/237,114

(22) Filed: Sep. 20, 2011

(65) Prior Publication Data

US 2013/0073057 A1 Mar. 21, 2013

(51) Int. Cl.
| | | |
|---|---|---|
| *A61F 2/78* | (2006.01) | |
| *A61F 2/60* | (2006.01) | |
| *A61F 2/28* | (2006.01) | |
| *A61F 2/30* | (2006.01) | |
| *A61F 2/80* | (2006.01) | |
| A61F 2/70 | (2006.01) | |
| A61F 2/76 | (2006.01) | |

(52) U.S. Cl.
CPC ... *A61F 2/80* (2013.01); *A61F 2/78* (2013.01); A61F 2002/705 (2013.01); A61F 2002/7615 (2013.01); A61F 2002/7887 (2013.01)
USPC .............. 623/33; 623/28; 623/32; 623/16.11; 623/23.48; 623/18.12; 623/23.44; 623/23.46; 623/36; 623/37

(58) Field of Classification Search
USPC ................. 623/20.21, 20.35–20.36
See application file for complete search history.

(56) References Cited

U.S. PATENT DOCUMENTS

| | | | | |
|---|---|---|---|---|
| 3,947,897 A | * | 4/1976 | Owens ........................ 623/11.11 |
| 3,992,725 A | | 11/1976 | Homsy | |
| 4,007,494 A | * | 2/1977 | Sauer ........................ 623/23.12 |
| 4,547,912 A | * | 10/1985 | Sherva-Parker ........... 623/16.11 |
| 4,634,446 A | * | 1/1987 | Kristinsson ..................... 623/33 |
| 4,743,264 A | * | 5/1988 | Sherva-Parker ................ 623/33 |
| 4,778,470 A | * | 10/1988 | Antebi ............................. 623/27 |
| 4,781,720 A | * | 11/1988 | Sherva-Parker ................ 623/27 |
| 5,041,137 A | * | 8/1991 | Nemoshkalov ............... 128/898 |
| 5,507,835 A | * | 4/1996 | Jore ................................. 623/36 |
| 5,531,793 A | * | 7/1996 | Kelman et al. ............. 623/16.11 |

(Continued)

FOREIGN PATENT DOCUMENTS

| | | |
|---|---|---|
| WO | WO 02-26158 | 4/2002 |
| WO | WO 2010-070614 | 6/2010 |

OTHER PUBLICATIONS

Attinger, C.E., et al., "Angiosomes of the Foot and Ankle and Clinical Implications for Limb Salvage: Reconstruction, Incisions, and Revascularization," *Plastic and Reconstructive Surgery*, vol. 117, No. 7S, Jun. 2006 Supplement, pp. 261S-293S.

(Continued)

*Primary Examiner* — David Isabella
*Assistant Examiner* — Jacqueline Woznicki
(74) *Attorney, Agent, or Firm* — Saliwanchik, Lloyd & Eisenschenk

(57) ABSTRACT

Embodiments of the invention include an implantable force distribution boot with hydraulic features that mimic the natural hydraulics of a joint. Further embodiments include an exterior prosthetic leg device having intermittent and/or variable electromagnetic features that can engage with magnetic blades on the implantable force distribution boot. In use, the exterior prosthetic leg can be maintained on a residual limb by magnetic force between the implanted blades and the exterior electromagnets. Also disclosed are surgical techniques for preparing a residual limb to better receive and adapt to a prosthetic device. The techniques include an improved surgical method for harvesting a vascularized glabrous skin free flap.

88 Claims, 25 Drawing Sheets

(56) References Cited

U.S. PATENT DOCUMENTS

| | | | |
|---|---|---|---|
| 5,571,208 A * | 11/1996 | Caspers | 623/32 |
| 5,591,233 A * | 1/1997 | Kelman et al. | 623/23.51 |
| 5,725,580 A * | 3/1998 | Cloutier et al. | 623/16.11 |
| 5,879,386 A * | 3/1999 | Jore | 623/16.11 |
| 5,894,181 A * | 4/1999 | Imlach | 310/90.5 |
| 5,904,722 A | 5/1999 | Caspers | |
| 6,123,716 A * | 9/2000 | Augustine et al. | 607/104 |
| 6,132,468 A | 10/2000 | Mansmann | |
| 6,197,065 B1 * | 3/2001 | Martin et al. | 623/23.17 |
| 6,224,623 B1 * | 5/2001 | Augustine et al. | 607/104 |
| 6,355,067 B1 * | 3/2002 | Bloebaum | 623/16.11 |
| 6,387,096 B1 * | 5/2002 | Hyde, Jr. | 606/60 |
| 6,482,238 B1 * | 11/2002 | Grundei | 623/32 |
| 6,599,321 B2 * | 7/2003 | Hyde, Jr. | 623/18.12 |
| 6,709,466 B1 | 3/2004 | Grundei | |
| 6,923,832 B1 * | 8/2005 | Sharkey et al. | 623/20.34 |
| 7,044,953 B2 * | 5/2006 | Capanni | 606/309 |
| 7,101,374 B2 * | 9/2006 | Hyde, Jr. | 606/60 |
| 7,223,293 B2 | 5/2007 | Kristensen | |
| 7,302,296 B1 | 11/2007 | Hoffer | |
| 7,374,577 B2 | 5/2008 | Kim et al. | |
| 7,850,740 B2 * | 12/2010 | Cox et al. | 623/37 |
| 7,909,883 B2 | 3/2011 | Sidebotham | |
| 7,922,773 B1 | 4/2011 | Kuiken | |
| 7,967,869 B2 | 6/2011 | Schulman et al. | |
| 7,972,384 B2 * | 7/2011 | Parsell | 623/23.48 |
| 2004/0193286 A1 | 9/2004 | Grundei | |
| 2005/0101693 A1 * | 5/2005 | Arbogast et al. | 523/122 |
| 2005/0119755 A1 * | 6/2005 | Kristensen | 623/18.11 |
| 2005/0171604 A1 * | 8/2005 | Michalow | 623/14.12 |
| 2005/0240283 A1 * | 10/2005 | Kania | 623/36 |
| 2006/0064169 A1 * | 3/2006 | Ferree | 623/17.12 |
| 2006/0293762 A1 * | 12/2006 | Schulman et al. | 623/32 |
| 2007/0150070 A1 * | 6/2007 | Kim et al. | 623/32 |
| 2007/0162150 A1 | 7/2007 | Fago et al. | |
| 2009/0005820 A1 * | 1/2009 | Bloebaum et al. | 606/302 |
| 2009/0198342 A1 * | 8/2009 | Parsell | 623/23.48 |
| 2009/0254196 A1 * | 10/2009 | Cox et al. | 623/33 |
| 2010/0152864 A1 | 6/2010 | Isaacson et al. | |
| 2010/0203155 A1 * | 8/2010 | Wei et al. | 424/549 |
| 2010/0268232 A1 * | 10/2010 | Betz et al. | 606/79 |
| 2011/0054408 A1 * | 3/2011 | Wei et al. | 604/175 |
| 2012/0116539 A1 * | 5/2012 | Armstrong et al. | 623/36 |

OTHER PUBLICATIONS

Dillingham, T.R., et al., "Use and Satisfaction with Prosthetic Devices Among Persons with Trauma-Related Amputations," *American Journal of Physical Medicine & Rehabilitation*, Aug. 2001, vol. 80, No. 8, pp. 563-571.

Gray, H., *Gray's Anatomy*, 1901, reprinted 1995, Barnes and Noble, 15th Ed., pp. 562-570.

Imanishi, N., et al., "Anatomical Study of Cutaneous Venous Flow of the Sole," *Plastic and Reconstructive Surgery*, Dec. 2007, vol. 120, No. 7, pp. 1906-1910.

NLLIC Staff, "Amputation Statistics by Cause: Limb Loss in the United States," National Limb Loss Information Center Fact Sheet, Rev. 2008.

Oh, S.J., et al., "Weight-Bearing Plantar Reconstruction Using Versatile Medial Plantar Sensate Flap," *Journal of Plastic, Reconstructive & Aesthetic Surgery*, 2011, vol. 64, pp. 248-254.

Russell, W.L., et al., "Limb Salvage Versus Traumatic Amputation," *Annals of Surgery*, May 1991, vol. 213, No. 5, pp. 473-480.

Stansbury, L.G., et al., "Amputations in U.S. Military Personnel in the Current Conflicts in Afghanistan and Iraq," *Journal of Orthopaedic Trauma*, Jan. 2008, vol. 22, No. 1, pp. 43-46.

Vasquez, T., et al., "Anatomic Study of Blood Supply of the Dorsum of the Foot and Ankle," *Arthroscopy: The Journal of Arthroscopic and Related Surgery*, Mar. 2006, vol. 22, No. 3, pp. 287-290.

Waters, P.M., et al., "Use of an Osteocutaneous Plantar Free Flap for Salvage of a Below-the-Knee Amputation in a Child: A Case Report," *Journal of Bone and Joint Surgery*, Jul. 1997, vol. 79, No. 7, pp. 1073-1075.

Yamada, T., et al., "Variations of the Arterial Anatomy of the Foot," *The American Journal of Surgery*, Aug. 1993, vol. 166, No. 2, pp. 130-135.

Yavari, M., et al., "Comparison of Sole to Palm Reconstruction Using the Combined Medical Plantar and Medial Pedis Free Flaps and Abdominal Pedicle Flap for Extensive Palm Injuries," *Acta Medica Iranica*, 2010, vol. 48, No. 4, pp. 214-217.

Zhang, M., et al., "Clinical Investigation of the Pressure and Shear Stress on the Trans-Tibial Stump With a Prosthesis," *Medical Engineering & Physics*, Apr. 1998, vol. 20, No. 3, pp. 188-198.

Ziegler-Graham, K., et al., "Estimating the Prevalence of Limb Loss in the United States: 2005 to 2050," *Archives of Physical Medicine and Rehabilitation*, Mar. 2008, vol. 89, No. 3, pp. 422-429.

* cited by examiner

IMPLANTABLE PROSTHETIC DEVICE FOR DISTRIBUTION OF WEIGHT ON AMPUTATED LIMB AND METHOD OF USE WITH AN EXTERNAL PROSTHETIC DEVICE

BACKGROUND OF INVENTION

Limb amputations have been part of humankinds' existence from its beginning as evidenced by hieroglyphics depicting techniques to fashion amputee prosthetics. Traumatic limb amputations were a common battlefield wound in the age of combat fought with swords and axes. Cautery of the residual limb or stump with hot oil or heated metal was the preferred method to stem the flow of blood on these ancient battlefields. It was not until the 1500's when Ambroise Pare demonstrated that ligation of the artery and vein with delayed or primary closure of the amputee wound provided superior healing and rehabilitation when compared to the cauterization techniques. Injury to or loss of extremities on the modern battlefield are particularly common today and is seen in 70.5 percent of all wounded soldiers. Within this group, 7.4 percent experienced amputation with explosive devices (explosive shock waves and shrapnel) accounting for 87.9 percent of the mechanism of injury.[1] Sadly, as the manner in which humankind maims itself on the battlefield has advanced, the management of amputations has changed little since Pare's revolutionary surgical management techniques. Amputations though are not unique to the battlefield. For civilians, in one study, the major traumatic reasons for lower extremity amputations involved blunt or penetrating trauma with motor vehicle accidents and gunshot wounds the two most common causes respectively.[12] Further, according to the National Limb Loss Information Center, vascular disease is the leading case of lower extremity amputation in the United States with trauma second. Overall, approximately 30 percent of all amputations are of a lower extremity.[2] As of 2005, approximately 1.6 million people lived with the loss of an appendage and this number is expected to double by 2050.13

One of the most difficult problems that a lower extremity amputee faces today is being able to transition to the use of a new prosthesis quickly. In some cases, patients take years to functionally adapt to their prosthesis. This delay in the use of the prosthesis is often due to the physiological changes that occur in the extremity during healing and afterwards during normal daily activities. This transition to use is further complicated by the skin covering the stump and the boney prominences within the stump preventing comfortable and consistent use of the prosthesis because the skin covering the amputation is not physiologically or anatomically suited for the pressures involved in ambulation. As a result, 25 percent of patients experience ulcerations of the stump and delayed wound healing from this physiological and mechanical skin mismatch on the amputee stump. Use of the prosthetic is further limited by pain and discomfort in the stump caused by the prosthesis, with amputees receiving on average a new prosthesis every two years.[3]

These problems are further complicated by marked variation in the surgical amputation techniques and socket manufacturing processes, both of which are typically performed by skilled artisans. Regardless of how advanced the prosthesis may be, if the amputee cannot use it because the stump is prepared anatomically and physiologically incorrect, then it is worthless. For these reasons, it seems evident that attempts to reconstruct or transplant the evolutionarily adapted weight-bearing and friction-tolerating glabrous skin of the foot to the amputee stump would help prevent these complications.

The successful use of vascularized plantar glabrous skin free flaps in reconstruction of like skinned areas has been documented, including its use on a below the knee amputation (BKA).[4,5,6] These successes have been achieved because the vascular anatomy of the foot and its plantar surface (i.e., sole of the foot) have been well documented through dissection and angiographic studies.[7,8,9,10,11] These studies have demonstrated that the glabrous skin and deep muscles of the plantar surface of the foot receive their blood supply from the posterior tibial artery (PTA) and its distal divisions—the medial and lateral plantar, plantar arch and metatarsal branches. The PTA also supplies the medial calcaneus region and has lateral anastomatic connections with the external Calcanean, the terminal branches of the posterior Peroneal artery (PPA) through the PTA's internal Calcanean branches. Distally the Communicating artery from the Dorsalis Pedis artery passes between the first two heads of the Dorsal Interosseous muscle then joining with the Plantar Arch. Typically, this artery is ligated as it is encountered during the development of the plantar flap, just proximal and between the first and second metacarpal-phalangeal joints.

It is equally important to consider reconstruction of the hydrodynamic function of the skeletal system after amputation. With the loss of the fluid filled ankle joint in below knee amputations and the loss of the knee joint and ankle joint in above the knee amputations, the normal non-compressible fluid hydraulic system of the axial skeleton is lost. As a result, expecting the amputee to walk on a boney stump inserted into a prosthetic socket can be unreasonable, as evidenced by the difficulty often experienced with the transition and use of a new prosthesis.

In addition to the problems of learning to walk with a prosthesis, the methods and devices used to hold the prosthesis in place on the residual limb present a whole different set of problems. The manner in which a prosthetic device is attached to the residual limb can determine the amount of control the amputee has over the prosthesis and, consequently, their ease and range of movement. Patients have utilized a variety of belts, bands, straps, cuffs, harnesses, sockets, suction sleeves and the like to secure a prosthesis against a residual limb. The disadvantage with most of these devices is that they are inconvenient and usually cause chafing, which leads to sores and abrasions and, in some cases, secondary skin infections. They can also impair circulation in the residual limb causing pain and tissue degradation. Other techniques involve the use of protruding skeletal extensions, where a rod or other mechanism is affixed to the terminal bone end of the residual limb. The extension protrudes from the residual limb to be attached to a prosthetic device. The challenge with these devices is the difficulty in attaining a permanent intact skin-prosthesis interface. If the tissue does not heal properly around the extension, the exit wound can remain open and subject to infection and other problems.

There is a need to overcome the dysfunctional, post-surgical-anatomical deficiency exhibited by most currently used prostheses. More specifically, there is a need for a system that replaces that portion of the non-compressible fluid hydraulic system lost with amputation. Such a system should distribute the weight and forces of ambulation over a larger area of the residual limb end. There is also a need for an improved plantar surface free flap harvesting technique, which will provide the proper weight bearing skin of the plantar surface to the residual limb. Finally, new methods and devices are needed for securing a prosthesis to a residual limb.

BRIEF SUMMARY

The embodiments of the subject invention successfully address the above-described disadvantages associated with the previously known prosthetic devices and their methods of use, and provide certain attributes and advantages, which have not been realized by these known devices. In particular, the embodiments of the subject invention provide novel and highly effective methods and devices for distributing the weight and forces of ambulation over the reconstructed amputee residual limb flap and boney stump. More specifically, the embodiments of the subject invention provide an implantable, orthopedic, hydrodynamic amputee prosthesis designed to provide a non-compressible space that distributes the weight and force of walking over the entire surface of the residual limp. Advantageously, the devices and methods disclosed herein improve the dynamic interaction between the newly reconstructed residual limb and the external walking prosthesis and prevent the otherwise dysfunctional boney stump from receiving all the weight of walking on a single point.

Embodiments of the subject invention provide a bladder or variable density semi-solid that individually or together because of its non-compressibility or variable compressibility acts hydraulically to accept the forces and then transfers the weight and force of walking evenly over the reconstructed stump. This hydraulic system (as in, for example, a natural fluid filled joint) allows for the force of walking to be directed to the bone, so the axial skeleton now accepts the weight and force of walking instead of the amputee stump skin. This system provides for a more functional weight bearing and walking surface. In particular embodiments, an implantable prosthesis will in effect reconstruct the natural hydraulic damping and walking dynamics to the residual boney stump of the amputated prosthesis. This can be a critical component of any reconstruction, which will, ideally, restore the role of the skeleton in absorbing the dynamic force of walking.

In accordance with the embodiments of the subject invention, the problem of weight distribution on a reconstructed stump is solved by an implantable force-distribution boot internally fixed to the terminal end of the residual limb bone or bones stump. The boot acts as a hydrodynamic force distributor and effectively replaces the natural hydraulic system of the joints lost with the amputation.

The problem of providing a physiologically and anatomically suited covering for the terminal end of the residual limb is solved by using a plantar skin "free flap". Embodiments of the subject invention provide efficient and rapid techniques for harvesting a significant portion of the plantar skin and transplanting the resultant free flap to the terminal end of the residual limb. In particular, the harvesting techniques disclosed include procedures for preserving the integrity of the flap vasculature and enervation of the tissue for re-implantation.

Once the residual limb has been properly prepared, the next step is fitting and using a prosthetic limb. Embodiments of the subject invention include a prosthetic limb attachment that utilizes ferromagnetic materials, magnets and a controllable electromagnetic mechanism. More specifically, embodiments include implanted ferromagnetic materials, magnets and/or electromagnetic devices that are fixed to the internal supporting struts that attach the implanted hydrodynamic force-distribution boot to the bone stump. Externally in the prosthesis socket, there can be aligned electromagnets that are controlled by sensor switches that relay on-off signals to the electromagnets during the walking cycle. Further, to reduce or prevent ischemia of tissues, the electromagnetic devices can be regulated by the motion of the residual limb, which causes them to be activated only when needed to support the weight of the prosthesis during the leg swinging motion of walking. Embodiments of the prosthetic limb include proximity sensors located in the heel of the foot portion of the prosthesis. These sensors sense heel strike and heel lift that signals to turn the electromagnets off and on respectively. This is another unique aspect of the design that regulates operation of the electromagnets. When the limb can be supported or held in place by gravity or other forces, the electromagnets are deactivated, allowing perfusion of the skin with the force of walking distributed through the hydrodynamic boot to the bone. This electro-mechanic coupling process combined with the properly prepared plantar surface skin flap and reestablishment of the hydraulic system of walking (with the hydrodynamic boot) can reduce pain, tissue degradation and skin ulcerations. By allowing for longer periods of continuous use of the prosthesis, amputees will have more productive days unencumbered with the use of wheelchairs or crutches. This will allow the amputee to reintegrate into the work force and society in general.

As with many implanted devices, it is possible that these embodiments may not be lifetime devices. It is anticipated that additional unplanned surgeries on the residual limb may be necessary because of complications, discomfort, or unacceptable cosmetic outcomes. These additional surgeries can include implant removal with or without replacement, or they can include other surgical procedures as advancements in the device are made. Advantageously, the modularity provided by embodiments of the subject invention allows certain components to be removed, replaced, or upgraded if necessary. But, the device disclosed herein can provide a patient with a more convenient and comfortable alternative prosthesis that reduces overall stress on the residual limb, as well as the entire body.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. It should also be understood that the drawings presented herein may not be drawn to scale and that any reference to dimensions in the drawings or the following description are specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 7A illustrates a set-screw that combines an anchoring screw (proximal end) and external mounting screw (distal end). In certain embodiments, the set-screw is used to attach the terminal end of the amputated bone to an above-knee hydraulic dashpot. FIG. 7B illustrates a set-screw having a collar. FIG. 7C illustrates a modified set-screw that can engage with just a set-screw bore.

FIG. 9A shows a subperiosteal strut with a set-screw bore. FIG. 9B shows a subperiosteal strut with external threading on the sleeve.

FIG. 14A illustrates an embodiment wherein the sockets are bands that surround the terminal ends of the bones. FIG. 14B illustrates an embodiment wherein the sockets are cup-like receptacles into which the terminal bones ends are received. FIG. 14C illustrates an embodiment wherein the distance between the sockets is adjustable.

DETAILED DISCLOSURE

Figure 1:
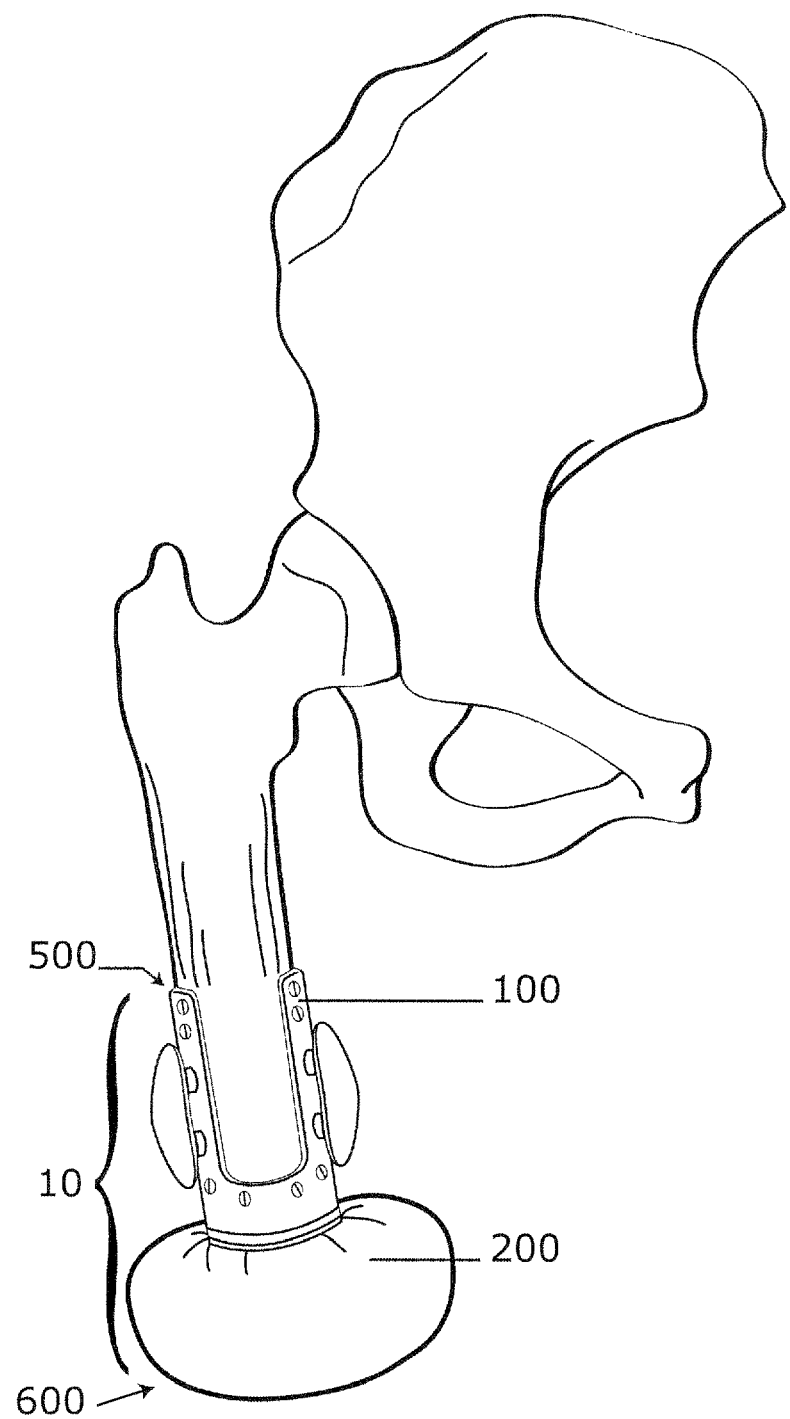
FIG. 1 is an illustration of an embodiment of a femoral subperiosteal strut and above-knee hydraulic dashpot combined to form a modular, implantable force-distribution boot. This illustration shows the force-distribution boot installed on the femur bone of an above-knee-amputation (AKA). This embodiment also shows the blades in a horizontal alignment.

The subject invention in general pertains to methods and devices for providing an amputee with a prosthetic limb system for comfortable, long-term ambulation. More specifically, the subject invention pertains to one or more embodiment(s) of an implantable prosthetic component, a surgical technique for preparing the residual limb and an external prosthetic limb that works with the implantable component.

The following description will disclose that the embodiments of the subject invention are particularly useful in the field of lower extremity amputations, in particular to devices used to provide ambulation to an amputee and methods for preparing a residual limb to receive an external prosthesis. However, a person with skill in the art will be able to recognize numerous other uses that would be applicable to the devices and methods of the subject invention. While the subject application describes a use with residual leg limbs, other modifications and uses that would be apparent to a person with skill in the art and having benefit of the subject disclosure are contemplated to be within the scope of the present invention.

In the description that follows, a number of terms used in relation to the field of surgical amputations are utilized. In order to provide a clear and consistent understanding of the specification and claims, including the scope to be given such terms, the following definitions are provided.

The terms "patient" or "amputee" as used herein, describes an animal, including mammals, to which the systems and methods of the present invention are applied. Mammalian species that can benefit from the disclosed systems and methods include, but are not limited to, humans, apes, chimpanzees, orangutans, monkeys; domesticated animals (e.g., pets) such as dogs, cats, guinea pigs, hamsters; veterinary uses for large animals such as cattle, horses, goats, sheep; and any wild animal for veterinary or tracking purposes.

The terms "surgeon" or "physician" as used in the subject invention are merely for literary convenience. The terms should not be construed as limiting in any way. The devices, apparatuses, methods, techniques and/or procedures of the subject invention could be utilized by any person desiring or needing to do so and having the necessary skill and understanding of the invention.

The term "anchoring screw" as used herein refers to any device that can be used to secure components of the subject invention to bone or other tissues within the body. Such devices can include, but are not limited to, medullary screws, cortico-medullary screws, intramedullary screws, entramedullary screws, hollow cortical screws, self-tapping screws, non-self tapping screws, compression plate compatible screws and similar devices. It can also include, but is not limited to, adhesives, bone-pastes, tapes or other winding material, or other types of biocompatible substances or devices for attaching components to bone or other tissues.

Also, as used herein, and unless otherwise specifically stated, the terms "operable communication," "operable connection," "operably connected," and "cooperatively engaged" or derivations thereof mean that the particular elements are connected in such a way that they cooperate to achieve their intended function or functions. The connection or engagement may be direct, or indirect, physical or remote.

Finally, reference is made throughout the application to the "proximal end" and "distal end." As used herein, the proximal end is that end nearest the hip joint of an amputee. Conversely, the distal end of the device is that end furthest from the hip joint of an amputee.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures, which show certain embodiments of the subject invention, on which the same reference numerals are used throughout to indicate the same or similar components. With reference to the attached figures, it can be seen that the embodiments of the subject invention comprise in general a subperiosteal strut 100 and a hydraulic dashpot 200 that can be operatively connected to create an implantable force-distribution boot 10. In further embodiments, the force-distribution boot can be operatively engaged with an external prosthetic limb 20. In specific embodiments, the force-distribution boot and the external prosthetic limb can be operatively engaged by the use of intermittent and/or variable electromagnetic forces created between components on each of these devices.

Also disclosed herein are procedures for transfer and implantation of glabrous skin in the form of a vascularized plantar free flap (VPFF) on lower extremity amputee residual limbs. The use of this procedure is not imperative to the success of the implantable prosthetic embodiments described herein, but would enhance the overall function by providing an adaptable and durable surface for its long-term function. Embodiments of this procedure include techniques for harvesting a plantar myocutaneous free flap that can be inset into the residual limb terminal end. The disclosed procedures provide a larger durable free flap for greater coverage of the residual limb terminal end and improved vascularization and re-enervation for a sensate transplantation.

Figure 11:
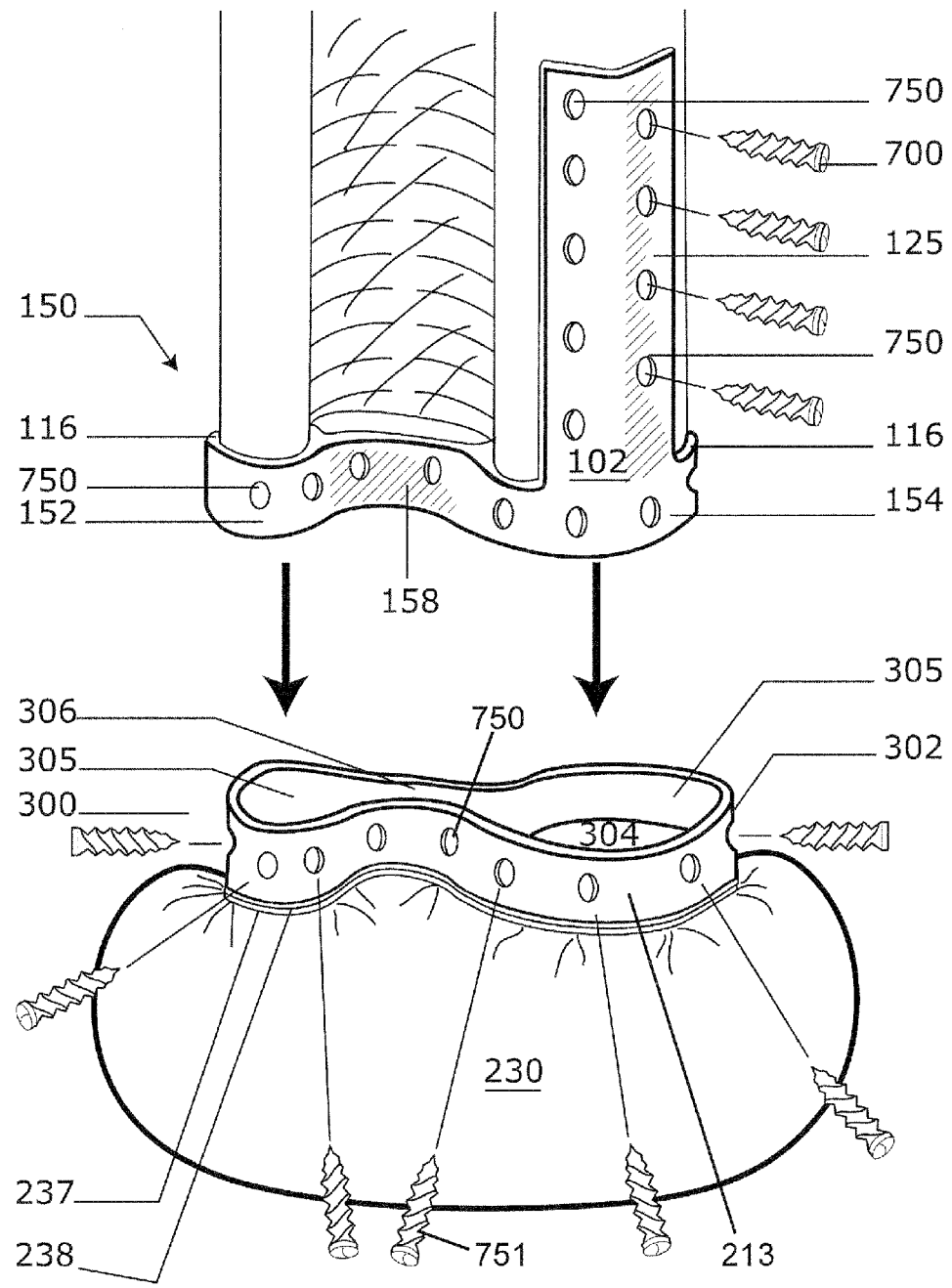
FIG. 11 shows a perspective view of an embodiment of a tibial-fibial subperiosteal strut prior to insertion into an embodiment of a below-knee hydraulic dashpot. In this embodiment, the below-knee dashpot is designed with a dual socket receiver for cooperatively engaging with the tibial-fibial subperiosteal strut.

I. Force Distribution Boot:

With regard to the force-distribution boot 10, FIG. 1 shows a generalized example attached to the terminal end of an amputated bone. In FIGS. 1 and 11, it can be seen that a subperiosteal strut 100 can act as a support structure that engages with the hydraulic dashpot 200, which is distal 600 to the subperiosteal strut. The subperiosteal strut is, in general, a bracket-like structure that can be attached around or to the terminal end of a bone(s) in a residual limb. Depending upon the location of the amputation, the residual limb can have a single terminal bone end, such as in the case of an above-knee-amputation (AKA), or two terminal bone ends, such as in the case of a below-knee amputation (BKA).

In cases where there has been an AKA, a femoral subperiosteal strut 102 can be utilized. FIGS. 2, 3, 6, 9A, and 10 illustrate one embodiment of a femoral subperiosteal strut according to the subject invention. In this embodiment, a tubular sleeve 105 has a diaphragm 110 disposed therein that separates the interior space of the sleeve into a femur socket 115 that opens at the proximal end 500 and a set-screw bore 120 that opens towards the distal end. The height of the femur socket from the diaphragm to the top of the femur socket wall 116 can vary depending upon numerous factors, such as, for example, the quality and/or stability of the terminal bone end, the material utilized for the sleeve, dimensions of the bone, and other factors that would be understood by a person with skill in the art. Ideally, the height of the femur socket wall is sufficient to provide support to the bone and adequate attachment to the bone.

The femur socket can receive the terminal bone end, which can abut the diaphragm and be held in place with one or more, preferably two or more, anchoring screws 700. Anchoring screws and their use in the body are well-known in the art. To facilitate the anchoring screws, the femur socket end of the sleeve, can have appropriately placed screw holes 750. Ideally, the anchoring screws are placed substantially opposite each other around the periphery of the femur socket or with maximum available distance therebetween. In an alternative embodiment, there is a plurality of screw holes 750 around the periphery of the femur socket 115 from which a surgeon can select to secure the femur within the femur socket. FIG. 9 illustrates one example of this embodiment. Thus, in those circumstances, where it may not be possible or necessary to place anchoring screws opposite each other, a surgeon can select the appropriate placement from the plurality of screw holes.

In one embodiment, one or more stanchions 125 extend proximally from the femur socket wall 116, such as shown, for example, in FIGS. 2, 3, 9A, and 10. The stanchions can be a separately attached component or be formed as part of the femur socket wall, as shown in the FIG. 10. The length of the stanchions can vary, but should be sufficient to provide support and attachment to the bone. In one embodiment, a stanchion is a rigid extension or attachment that extends, in general, parallel to the bone. In one embodiment, there is more than one stanchion, each of the same length. In an alternative embodiment, there is more than one stanchion and they have different length(s). In one embodiment, a stanchion has a length sufficient to include at least one, preferably two, screw holes. In a further embodiment, a stanchion has a length sufficient to include the anchoring screw hole(s), as well as supports for a blade 800, as shown, for example, on FIGS. 2, 3, 9A, and 10 and will be discussed in more detail below.

Figure 9A:
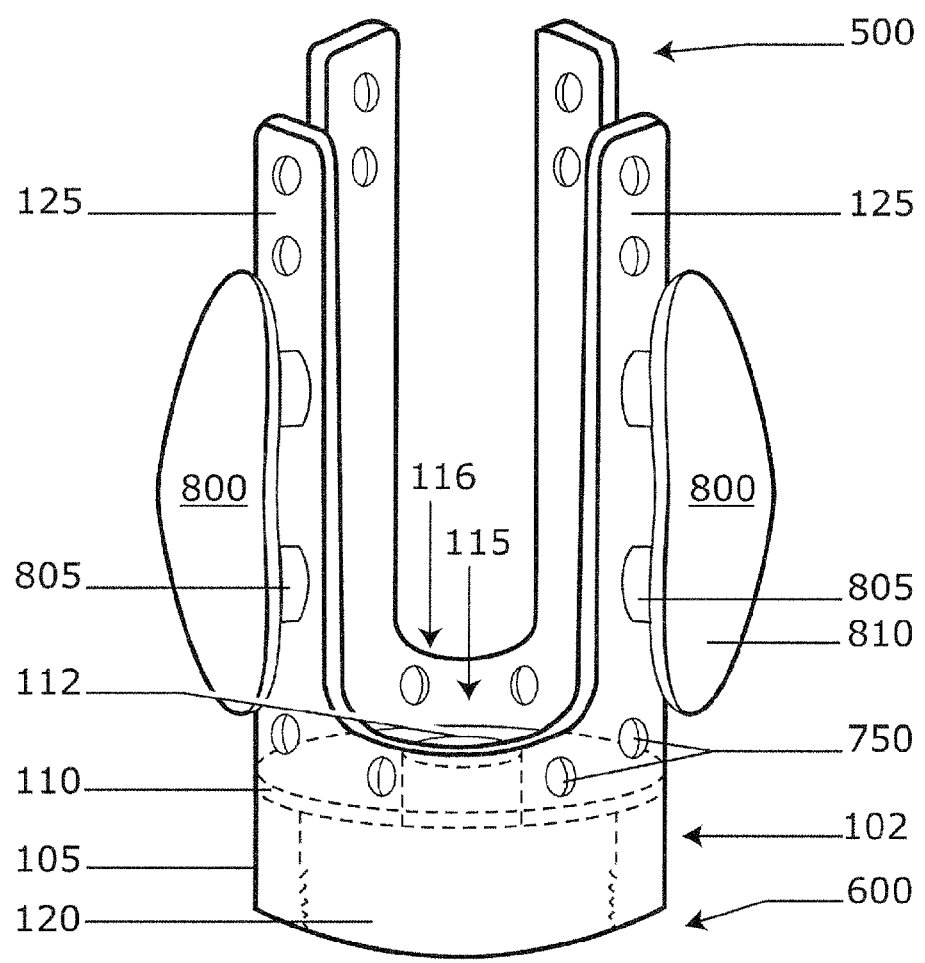
FIGS. 9A and 9B show perspective views of embodiments of a subperiosteal strut.

There can also be multiple stanchions extending from the femur socket wall. In one embodiment, there is at least one. In a more preferred embodiment, there are at least two stanchions. FIG. 9A illustrates an embodiment having four stanchions. A person with skill in the art, having benefit of the subject disclosure, would be able to determine an appropriate number and length for one or more stanchions.

The materials that can be utilized for a subperiosteal strut are preferably non-reactive and/or biocompatible materials capable of long-term in vivo use. Such materials can include, by way of non-limiting examples, various types of metals, metal alloys, plastics, ceramics, naturally-derived products, or combinations thereof. More specific examples can include, but are not limited to, titanium, cobalt-chromium-molybdenum alloy, steel, titanium-carbide-coated stainless steel, nylons, polyethylenes, hydroxyapatite (phosphocalcic ceramic), bone fusion matrix materials, or combinations of these or other materials that are suitable for in vivo use. The selection of an appropriate non-reactive and/or biocompatible material is within the competence of those skilled in the art. It is contemplated that such modifications are within the scope of the subject invention.

Figure 7A:
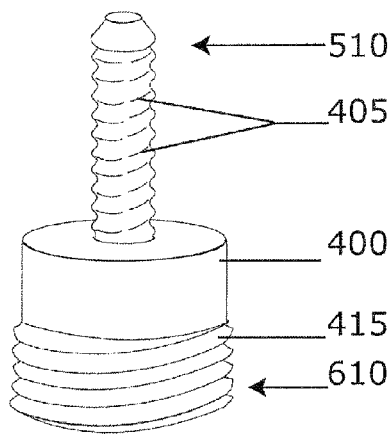
FIGS. 7A, 7B, and 7C show illustrations of embodiments of set-screws.
Figure 10:
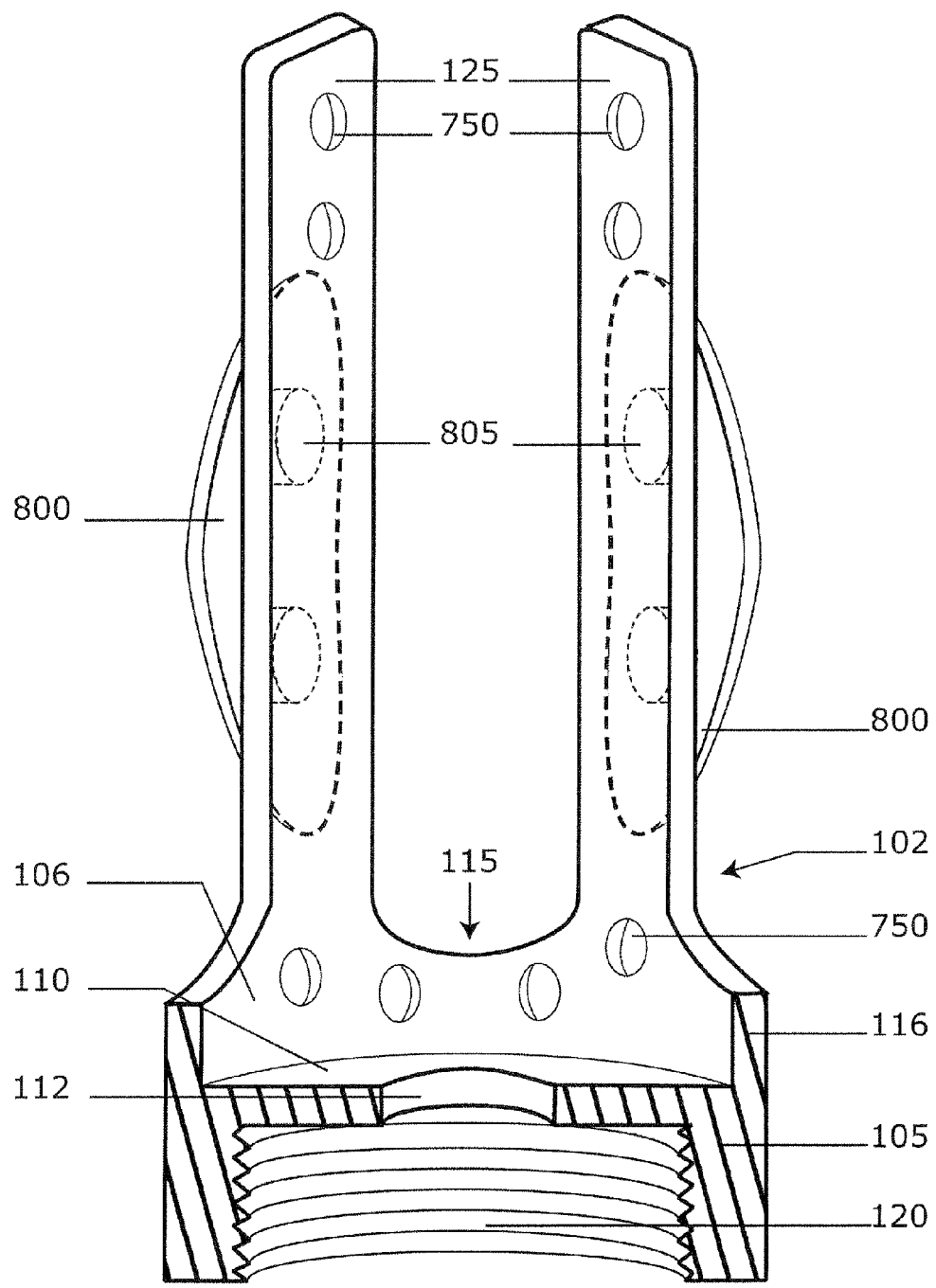
FIG. 10 shows a cross-sectional perspective view of an embodiment of a subperiosteal strut with vertically aligned blades.

To assemble an embodiment of the force distribution boot, the femoral subperiosteal strut is operably connected to an above-knee hydraulic dashpot 250. In one embodiment, the attachment of the above-knee hydraulic dashpot 250 to the femoral subperiosteal strut is accomplished by using a dual-end set-screw 400 between the components, such as the one shown, for example, in FIGS. 7A and 7B. A dual-end set-screw can have the same or different diameters on the proximal side 510 and the distal side 610. In one embodiment, the proximal side 510 has a smaller diameter than the distal side 610. In a more specific embodiment, the proximal side of the dual-end set-screw is configured with anchoring screw threads such as, for example, intermedullary or intramedullary screw threads 405 and the distal side is configured with machine threads 415. In a further embodiment, the diaphragm has a set-screw port 112, an example of which is shown in FIGS. 8, 9A, and 10, to accommodate the dual-end set-screw. The length of the dual-end set-screw and/or either side of the dual-end set-screw can vary depending upon the dimensions of the sleeve and/or the length of the residual bone remaining within the residual limb, as will become apparent below.

Figure 2:
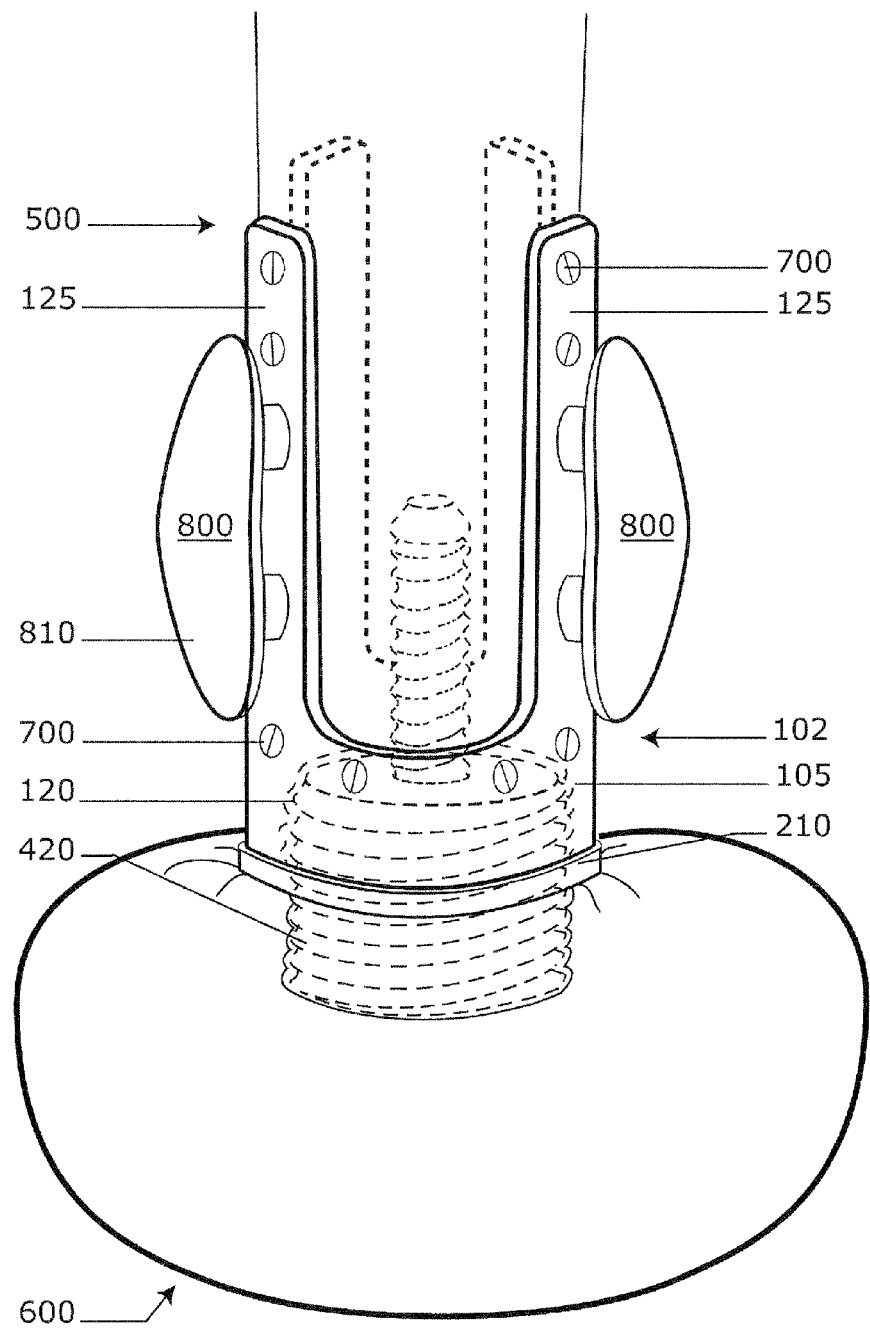
FIG. 2 is an enlarged perspective view of the embodiment of the force-distribution boot installed on the femur bone of an above-knee-amputation (AKA).

With this embodiment, the dual-end set-screw is placed into the set-screw bore 120, an example of which is shown in FIGS. 2, 9A, and 10, so that the proximal end of the dual-end set-screw will protrude from the set-screw port 112 in the diaphragm 110 into the socket receiver 115. In one embodiment, the set-screw bore 120 has threads complementary to the machine threads 415 on the distal side 610 of the dual-end set-screw, so that the distal side of the dual-end set-screw can be screwed into the set-screw bore, as shown for example in FIG. 12. In an alternative embodiment, the distal side 610 can be configured to slide into the set-screw bore and can have only partial threading that engages with the set-screw bore, or threading only near the most distal portion that does not engage with the set-screw bore, as shown, for example, in FIG. 9A. In a further embodiment, the depth of the set-screw bore is such that the distal side 610 of the dual-end set-screw 400 will extend beyond the distal end 600 of the tubular sleeve 105. This can provide an external mounting screw portion 420, shown, for example, on FIG. 2, extending from the sleeve after the dual set-screw is sufficiently screwed into, slid into, or otherwise, engaged with, the set-screw bore 120.

The proximal side of the dual-end set-screw 400, having the intramedullary threads, can be screwed into the terminal end of the residual bone, so that it anchors within the intramedullary space. This can be done simultaneously as the set-screw is being screwed into the set-screw bore. Alternatively, the distal side of the set-screw can be fully or partially engaged with the set-screw bore, then the proximal end of the set-screw, with the attached subperiosteal strut, can be screwed into the intramedullary space. Ideally, the terminal end of the residual bone and the distal end of the set-screw will abut against their respective sides of the diaphragm 110 to achieve maximum support. However, this is not a required configuration and in some circumstances may not be possible. If necessary, spacers or washers 417, known to those with skill in the art, can be utilized between the bone and the diaphragm, such as those shown, for example, in FIG. 7C.

Figure 7B:
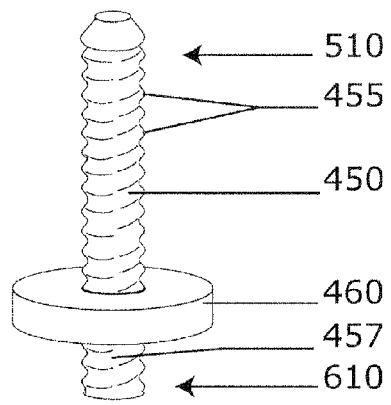
Figure 7C:
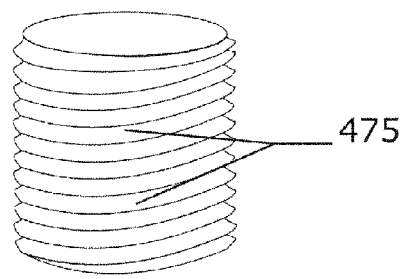
Figure 7D:
FIG. 7D shows an illustration of a spacer according to embodiments of the subject invention.
Figure 8:
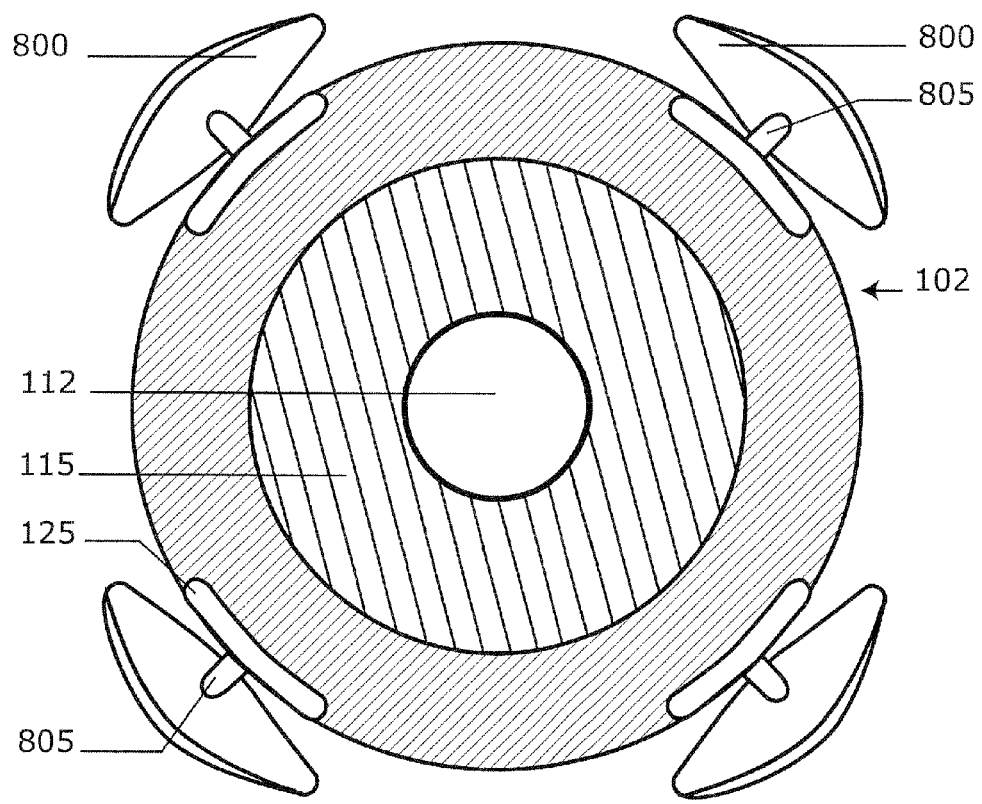
FIG. 8 shows a top plan view of an embodiment of a subperiosteal strut with attached blades in a vertical alignment. Also seen in this view is the central set-screw bore.
Figure 9B:
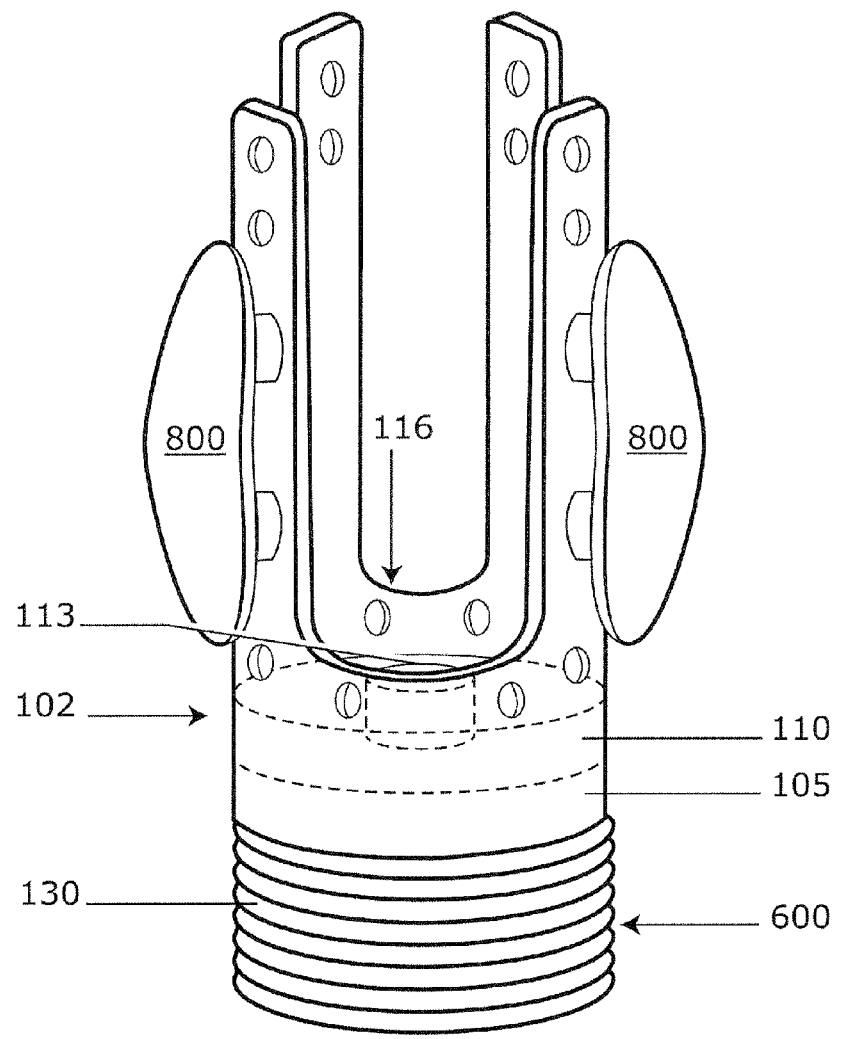

In an alternative embodiment the subperiosteal strut and the above-knee hydraulic dashpot are coupled utilizing a combined collared set-screw 450, shown, for example, in FIG. 7B, and a threaded sleeve 130, shown, for example, in FIG. 9B. The collared set-screw can be similar to the dual-end set-screw, in that the proximal side 510 can be configured with intramedullary threads 455 and the distal side 610 can be configured with machine threads 457. Each side of a collared set-screw can have the same or different diameters. In one embodiment, the proximal side 510 and distal side 610 have the same or similar diameter. In a further embodiment, there is a rigid or semi-rigid collar 460 between the two types of threading. The length of the collared set-screw and/or either end of the collared set-screw can vary depending upon the dimensions of the sleeve, the thickness of the diaphragm, the length of the residual bone remaining within the residual limb, and other factors known to those with skill in the art.

In a further embodiment, the set-screw port 112 in the diaphragm 110 is threaded. As described above, the set-screw port can go through the diaphragm and communicate the socket receiver 115 with the set-screw bore 120. In an alternative embodiment, the set-screw port does not go through the diaphragm, but, is a depression or hole 113 that opens into the socket receiver, as illustrated, for example, in FIG. 9B. The distal side of the collared set-screw can be coupled with the threaded set-screw port. In a further embodiment, the collar abuts the diaphragm, when the collared set-screw is fully screwed into the set-screw port.

In order to secure the terminal end of the residual bone into the femoral subperiosteal strut, the proximal side of the collared set-screw 450, having the intramedullary threads, can be screwed into the terminal end of the residual bone, so that it anchors within the intramedullary space. This can be done simultaneously as the collared set-screw is being screwed into the set-screw port. Alternatively, the distal side of the set-screw can be fully or partially engaged with the set-screw port, then the proximal end of the set-screw, with the attached subperiosteal strut, can be screwed into the intramedullary space. While the use of the collared set-screw can be beneficial in securing the bone to the subperiosteal strut, the threaded sleeve 150 can be used alone. Particularly if sufficient anchoring screws are utilized to secure the terminal bone end in the femur socket 115 and to the one or more stanchions 125. Ideally, the terminal end of the residual bone will abut against the diaphragm and/or the collar to achieve maximum support. However, this is not a required configuration and in some circumstances may not be possible. If necessary, various spacers or washers, known to those with skill in the art, can be utilized between the bone and the diaphragm, such as, for example, one shown in FIG. 7C. It is also possible for the femoral subperiosteal strut to be affixed to the residual bone without the use of a dual-end set-screw or a collared set-screw. Thus, the femoral subperiosteal strut can be affixed to the bone by use of only the anchoring screws. An alternative embodiment utilizes a modified set-screw 475, which is similar to a dual-end set-screw, but lacks the proximal end with intramedullary threads and has only the distal end 610 with machine threads, as shown, for example, in FIG. 7C. The modified set-screw can engage with the set-screw bore and can negate the necessity for a set-screw port 112.

The factors that can be considered by those skilled in the art with regard to the choice of materials for the components of the subject invention have been discussed above and are reasserted here with regard to the dual-end set-screw and the collared set-screw. Such material modifications to the dual-end set-screw and/or the collared set-screw, as would be apparent to a person skilled in the art having benefit of the subject disclosure, are deemed to be within the scope of the present invention.

In situations where a below-knee-amputation (BKA) has been performed, there are usually two terminal bones, the tibia and fibula in human patients, within the residual limb. FIGS. 11, 12, 14 and 15 illustrate one embodiment of a tibial-fibial subperiosteal strut 150 that can be utilized to stabilize these residual bone ends and attach them to a hydraulic dashpot 200. More specifically, the tibial-fibial subperiosteal strut can be used to attach the terminal bone ends to a below-knee hydraulic dashpot 300.

In one embodiment shown, for example, in FIGS. 11, 12, 14, and 15, the tibial-fibial subperiosteal strut has a fibial socket 152 and a tibial socket 154. In a further embodiment, the tibial socket is generally justaposed with the fibial socket. The fibial socket 152 can receive the terminal bone end of the fibula and the tibial socket 154 can receive the terminal bone end of the tibia. In one embodiment, these sockets 152, 154 are, in general, bands that surround the terminal bone ends. In an alternative embodiment, the sockets 152, 154 are cup-like openings into which the terminal bone ends can be seated against a socket floor 156, an example of which is shown in FIG. 14B. Typically, the tibia bone has a larger diameter than the fibia bone in human patients and can vary between patients. Therefore, the sizes or diameters of the tibial and fibial sockets can vary depending upon the diameter of these bones in a particular patient. In one embodiment, the tibial socket is larger than the fibial socket.

Figure 15:
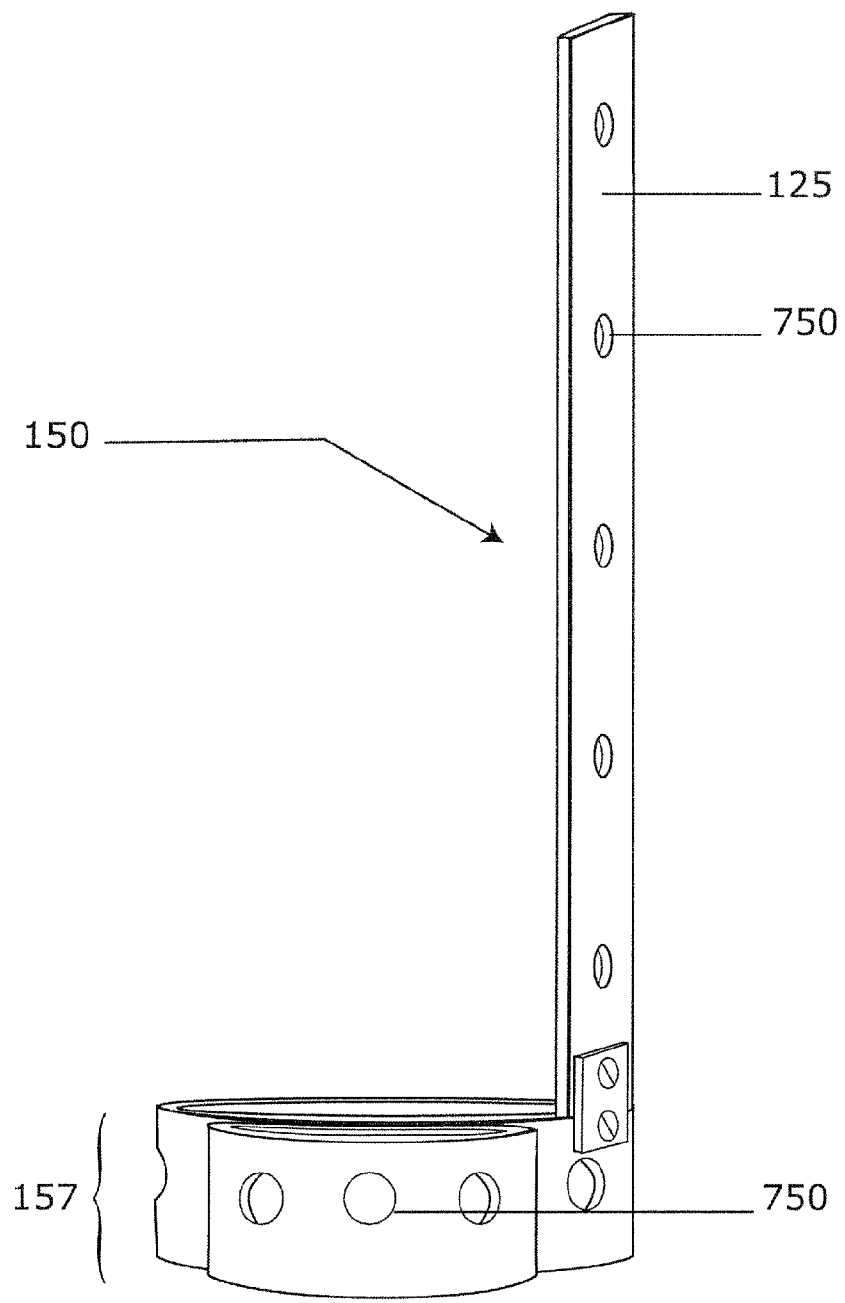
FIG. 15 is a side view of the tibial-fibial subperiosteal strut, with the fibial socket receiver foremost.

The height 157 of the tibial and/or femoral socket, as shown by way of example in FIG. 15, can vary depending upon numerous factors, such as, for example, the quality and/or stability of the terminal bone end, the material utilized for the sockets, dimensions of the bone, and other factors that would be understood by a person with skill in the art. Ideally, the height of the tibial and femoral socket walls is sufficient to provide support and adequate attachment to the bone. A person with skill in the art, having benefit if the subject disclosure, would be able to determine an appropriate height for tibial-fibial subperiosteal strut 150. It is contemplated that such variations, as would be made to the tibial-fibial subperiosteal strut to accommodate specific patients, would not deviate from the scope of the invention.

Figure 12:
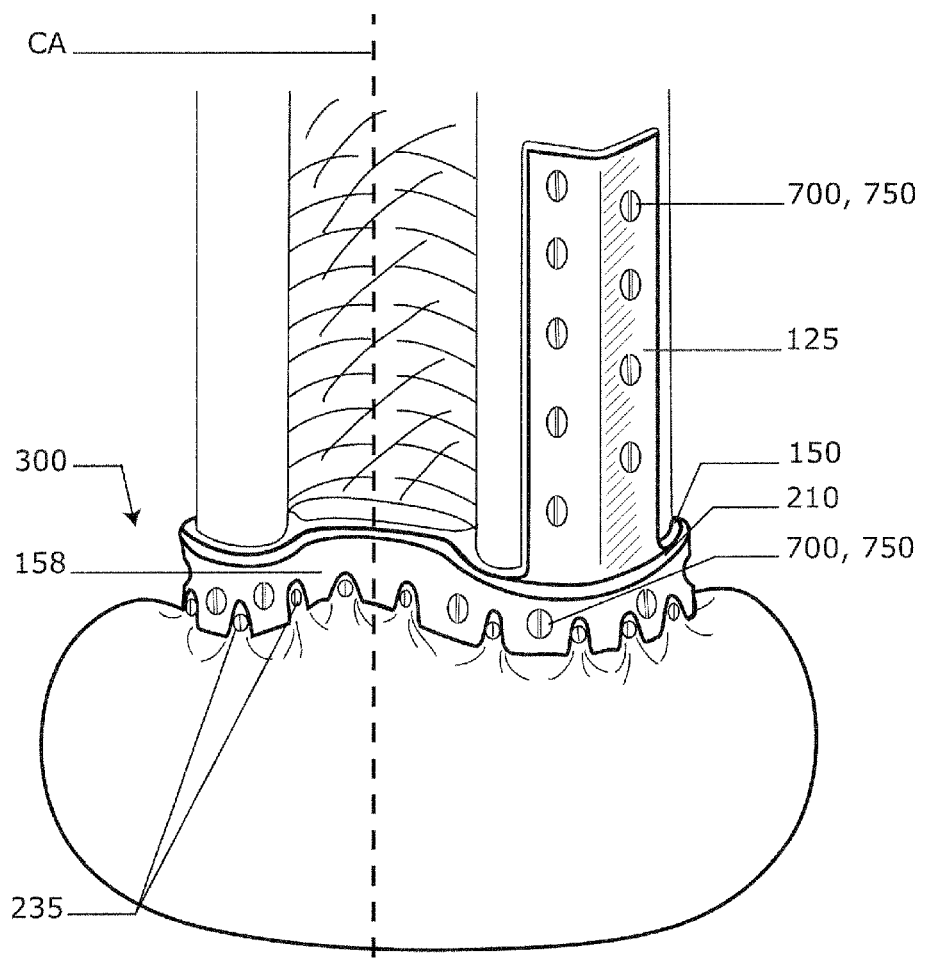
FIG. 12 shows a perspective view of an embodiment of the tibial-fibial subperiosteal strut inserted into a below-knee hydraulic dashpot.

In a further embodiment, the tibial and fibial sockets are joined together by a support bridge 158, such as shown, for example, in FIGS. 11, 12 and 14. The support bridge can act to connect the tibial and fibial sockets. In one embodiment, the support bridge 158 maintains the tibia and fibia at an appropriate distance, after they are inserted into their respective sockets. Thus, the length of the support bridge 158, and the distance between the tibial and fibial sockets can vary depending upon a variety of factors that would be understood by a person skilled in the art. Some of the factors that can be considered for the length of the support spacer include, by way of non-limiting examples, the length of the tibia and fibia, the normal, pre-amputated distance between the tibia and fibia, the diameter of the terminal ends, as well as other factors.

Figure 14A:
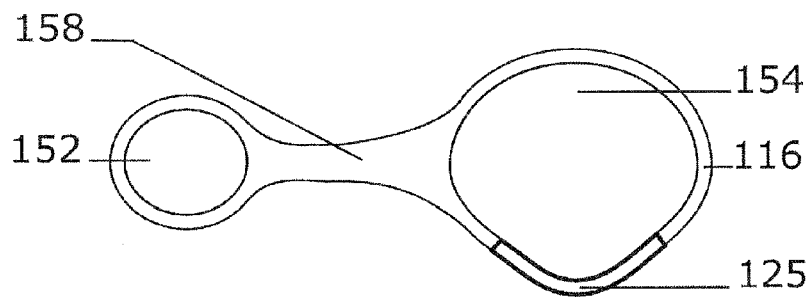
FIGS. 14A, 14B and 14C are top plan views of different embodiments of a tibial-fibial subperiosteal strut.
Figure 14B:
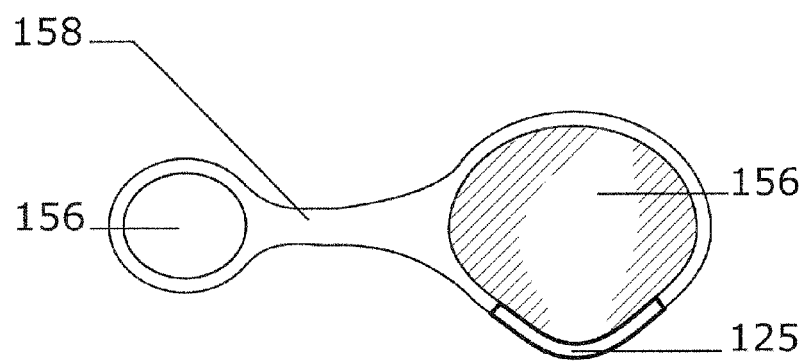

In one embodiment, the support bridge 158 is a solid, single piece of material fixedly attached between the two sockets. FIGS. 11, 14A and 14B illustrate examples of this embodiment, wherein the tibial and fibial sockets and the support bridge together form a single unified piece. In this embodiment, the surgeon would implant a tibial-fibial subperiosteal strut 150 with the appropriate socket dimensions and bridge size to accommodate the particular patient. Advantageously, this embodiment of a tibial-fibial subperiosteal strut provides a solid structure for supporting the terminal bone ends.

Figure 14C:
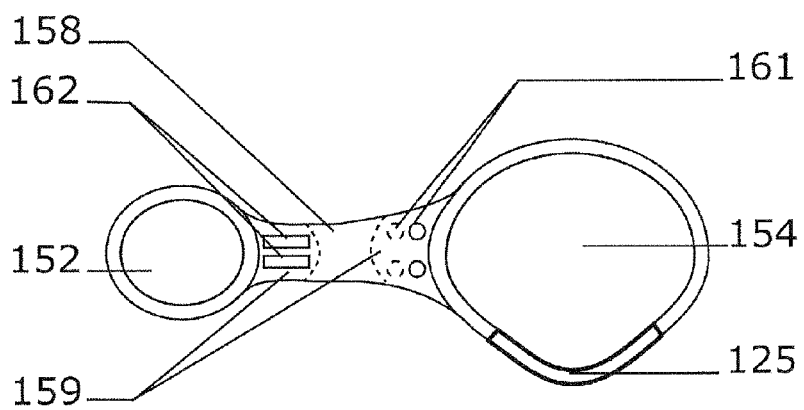

In some circumstances, it is expected that the distance between the tibia and fibia can or will change over time. Pediatric patients, for example, can require adjustment of the tibial-fibial subperiosteal strut as they grow. Other patients can also require adjustment as the residual limb and the terminal bone ends heal or settle into different positions over time. In these situations, it can be beneficial if the tibial-fibial subperiosteal strut can be adjusted. In one embodiment, the support bridge 158 is moveably attached to the fibial socket 152 and the tibial socket 154. In a further embodiment, the support bridge 158 is affixed to one or more fibial socket and tibial socket flanges 159, a non-limiting example of which is shown in FIG. 14C. In a still further embodiment, the support bridge 158 and socket flange(s) 159 have holes 161 or slots 162 that can be aligned and adjusted to provide the appropriate distance between the fibial and tibial sockets.

Once properly aligned, any of a variety of fastener types can be used to secure the socket flanges to the support bridge, such as, but not limited to, screws, bolts, rivets, pins, and the like. A person with skill in the art would be able to devise numerous techniques and devices for providing an adjustable support bridge attachable to the tibial and fibial sockets. It is contemplated that such variations can be utilized with the embodiments of the subject invention without departing from the scope of the invention.

As with the femoral subperiosteal strut 102 discussed above, the tibial-fibial subperiosteal strut 150 can receive the terminal bone ends and be held in place with one or more, preferably two or more, anchoring screws 700. Anchoring screws and their use in the body are well-known in the art. To facilitate the anchoring screws, the sockets 152 and 154 can have appropriately placed screw holes 750. Ideally, the anchoring screws are placed substantially opposite each other around the periphery of each of the sockets. In an alternative embodiment, there is a plurality of screw holes 750 around the periphery of both the fibial socket 152 and tibial socket 154 from which a surgeon can select to secure the fibia and tibia within the respective sockets. FIG. 11 illustrates one example of this embodiment. Thus, in those circumstances, where it may not be possible or necessary to place anchoring screws opposite each other, a surgeon can select the appropriate placement from the plurality of screw holes.

To further secure the terminal bone ends in the tibial-fibial subperiosteal strut 150, it may be necessary to have additional attachment structures. In one embodiment, one or more stanchions 125, such as shown, for example in FIGS. 11 and 15, extend proximally from the socket walls 116. In one embodiment, a stanchion is a rigid extension or attachment that extends, in general, parallel to the bone. In a further embodiment, a stanchion has one or more screw holes 750. The tibia is typically the larger of the two bones in the lower leg. As such, it can be more practical to use that bone for attachment structures, such as, for example, stanchions and one or more anchoring screws, or the like. However, it should be understood that, if necessary, the fibia could also be utilized. Thus, one or more stanchions could extend from the fibial socket wall as well. In a particular embodiment, there is a single stanchion extending from the tibial socket wall.

A stanchion can be a separately attached component, such as shown in FIG. 15, or be formed as part of the socket wall, as shown, for example, in the FIG. 11. The length of a stanchion can vary, but should be sufficient to provide support and attachment to the bone. In one embodiment, there is more than one stanchion, each of the same length. The multiple stanchions can be on the same socket or on different sockets. In an alternative embodiment, there is more than one stanchion and they have different length(s). In one embodiment, a stanchion has a length sufficient to include at least one, preferably two, screw holes. In a further embodiment, a stanchion has a length sufficient to include the anchoring screw hole(s), as well as supports for a blade 800, as shown, for example, on FIGS. 2, 3, 9, and 10 and discussed in more detail below. A person with skill in the art, having benefit of the subject disclosure, would be able to determine an appropriate number and length for one or more stanchions. Such variations are contemplated to be within the scope of the subject invention.

The factors that can be considered by those skilled in the art with regard to the choice of materials for the components of the subject invention have been discussed above and are reasserted here with regard to the tibial-fibial subperiosteal strut and stanchions. Such material modifications to the tibial-fibial subperiosteal strut and any associated stanchions, as would be apparent to a person skilled in the art having benefit of the subject disclosure, are deemed to be within the scope of the present invention.

To complete the assembly of the force distribution boot, the subperiosteal strut 100 is attached to a hydraulic dashpot 200, as shown in FIG. 1. The devices and methods of attachment can depend upon which type of subperiosteal strut is utilized. The hydraulic dashpot is designed to replace the natural joint hydraulic system that is lost with an amputation. Thus, the purpose of the hydraulic dashpot is to absorb and distribute the forces applied to the residual limb and, more particularly, to the terminal bone ends during ambulation. The fully assembled and implanted force distribution boot 10 is a biocompatible device that effectively replaces the one or more lost joint systems and acts as a hydrodynamic force distributor.

Referring to FIGS. 4, 5, 11 and 13, it can be seen that the components of a hydraulic dashpot 200 are, in general, a strut receiver 210 and a bladder 230. The design of the strut receiver can vary depending upon the type of subperiosteal strut to which it will be attached. Typically, the strut receiver has one or more openings on the proximal side for receiving a subperiosteal strut and the bladder can be attached so that it extends from the distal end.

Figure 4:
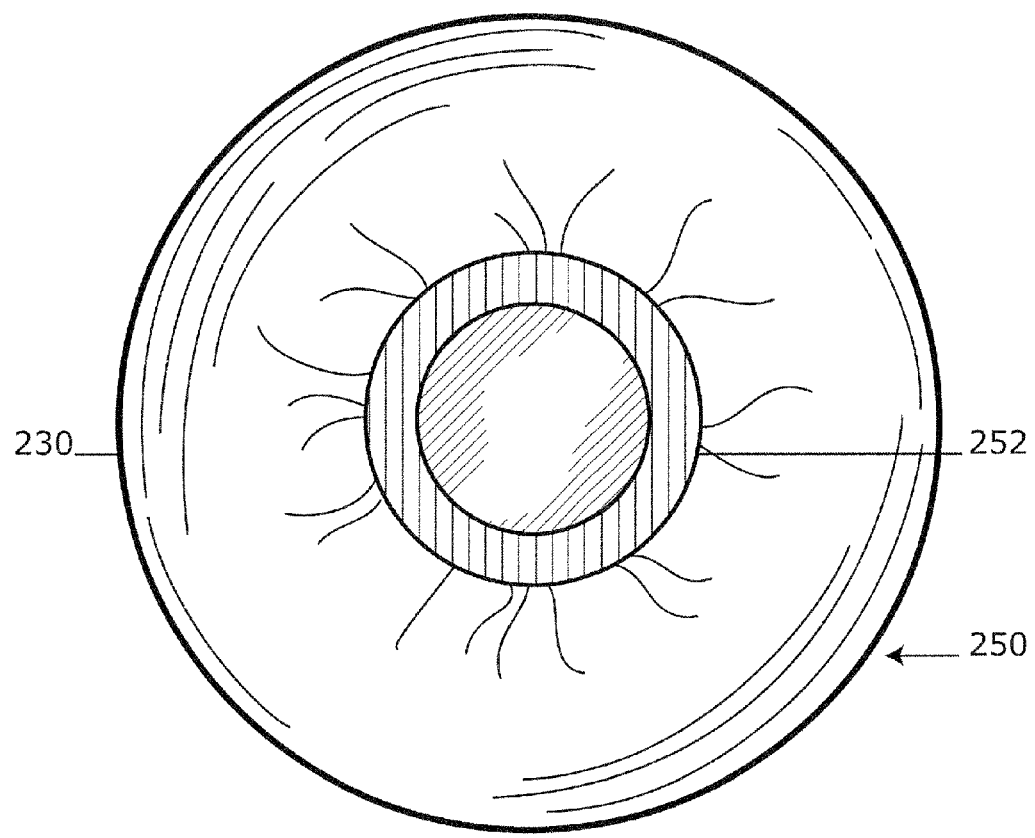
FIG. 4 shows a top view of an embodiment of the hydraulic dashpot. This embodiment has a single socket receiver designed to cooperatively engage with a set-screw.
Figure 5A:
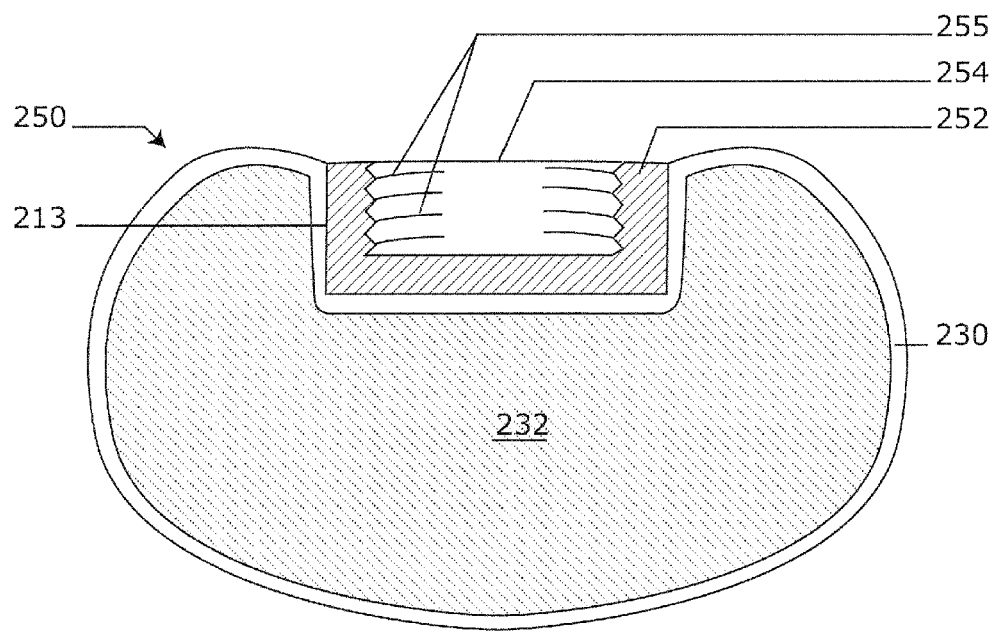
FIG. 5 shows a cross-sectional side view of the hydraulic dashpot.
Figure 5B:
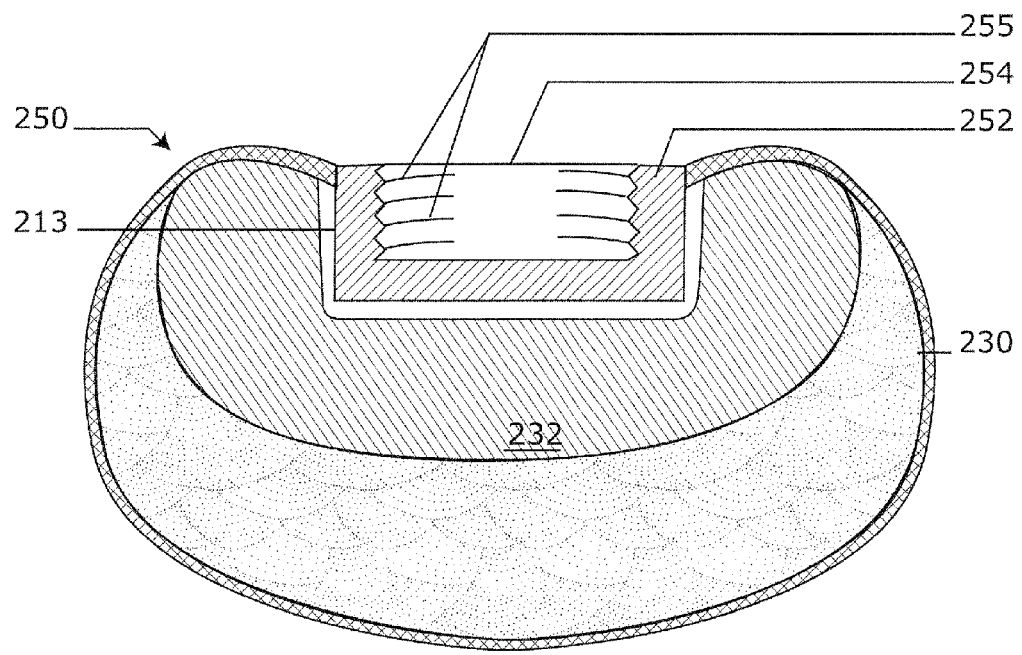

FIGS. 4 and 5 illustrate one embodiment of a hydraulic dashpot that can be operably attached to embodiments of a femoral subperiosteal strut 102. In this embodiment, the hydraulic dashpot utilizes a femoral strut receiver 252. In one embodiment, the femoral strut receiver is a rigid or semi-rigid device into which the external mounting screw portion 420 or the externally threaded sleeve 130, discussed above for the femoral subperiosteal strut, can be attached. In a further embodiment, shown, for example, in FIGS. 4 and 5, the femoral strut receiver is a generally tubular-shaped housing 254 having internal threads 255 compatible with those of the external mounting screw portion 420 and/or the externally threaded sleeve 130. In a specific embodiment, the circumferential shape of the receiver housing 254 is the same as, similar to, or otherwise compatible with the shape of the external mounting screw portion 420 or the externally threaded sleeve 130. In more specific embodiment, the receiver housing is circular.

With this embodiment, the external mounting screw portion 420 or the externally threaded sleeve 130 of the femoral subperiosteal strut embodiments described above can be screwed into the femoral strut receiver. Once completely screwed into place, it is anticipated that the threading between the components, as well as the surrounding tissues of the residual limb will assist in maintaining the hydraulic dashpot in the correct position and prevent it from coming unscrewed or loosened. However, a separate securing mechanism can also be used to ensure that it does not come unscrewed. A person with skill in the art would readily recognize any of a variety of inert and/or biocompatible techniques, devices and/or materials that could be employed to secure the femoral subperiosteal strut 102 within the femoral strut receiver 252. It is contemplated that such techniques, devices, materials, and variations thereof are within the scope of the present invention.

Figure 13:
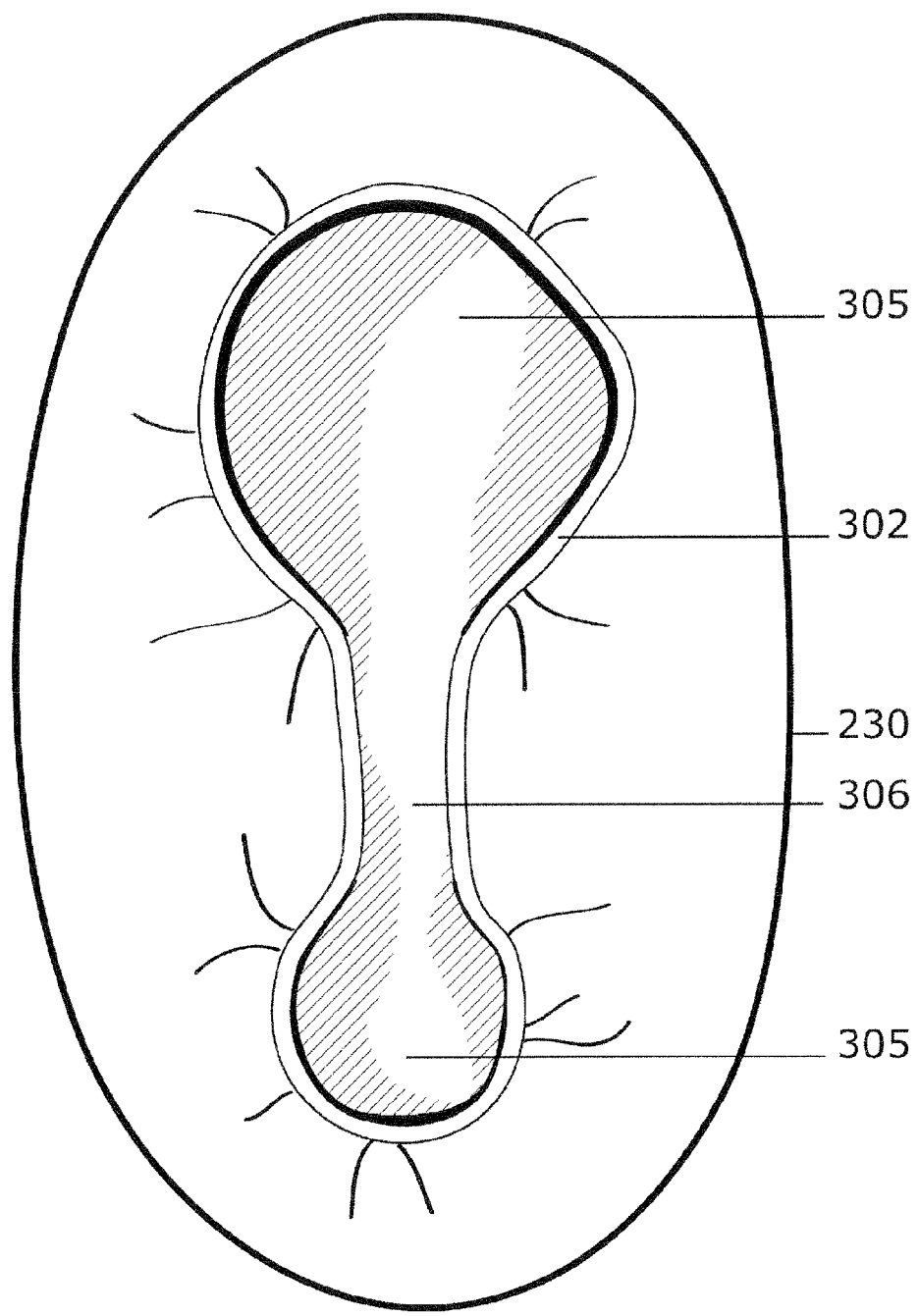
FIG. 13 is a top plan view of an embodiment of the below-knee dashpot showing a dual socket receiver.

In another embodiment, the hydraulic dashpot can be operably attached to embodiments of a subperiosteal strut 102, by use of a dual-strut receiver 302, an example of which is shown in FIGS. 11 and 13. In one embodiment, the dual strut receiver is a rigid or semi-rigid device to which the tibial-fibial subperiosteal strut 150 can be attached. In a further embodiment, shown, for example, in FIGS. 11 and 12, the dual strut receiver is a hollow chamber 304 having two socket-like or cup-like seats 305 at either end and a channel 306 therebetween that communicates the seats 305, providing an approximate "figure-8" shape. With this embodiment, the tibial-fibial subperiosteal strut is able to fit within the dual strut receiver, so that the sockets 152 and 154 fit into the respective, and appropriately sized, seats 305 and the support bridge 158 fits within the channel 306. Once properly seated, one or more securing set-screws 751 can be used in conjunction with screw holes 750 in the dual-strut receiver, as shown, for example, in FIG. 11, to hold the tibial-fibial subperiosteal strut into the dual-strut receiver.

The hydraulic features of the force distribution boot 10 are provided by the bladder 230. The bladder can be fixedly attached to at least some portion of, or the entire exterior surface 213 of, a strut receiver 210, so that it can distribute the forces exerted by a strut receiver 210, a subperiosteal strut 100, and the terminal bone end(s). The bladder, and/or the substances therein, can be comprised of a solid, semi-solid, liquid, semi-liquid, gel, gas, or combinations thereof. Ideally, the bladder, or the substances therein, comprise a material or materials that can absorb forces exerted by the terminal bone end(s) through a subperiosteal strut and a strut receiver, with minimal shape distortion. It can also be beneficial if the materials utilized in or for the bladder are non-compressible or minimally compressible. Further, since the bladder will be implanted, it can be preferable for the material(s) utilized for the bladder to be inert or otherwise biocompatible and capable of long-term or permanent in vivo use.

In one embodiment, the bladder 230 is a hollow balloon-like structure having an interior 232 filled with a liquid or semi-liquid material, such as, but not limited to, silicone gel, saline solution, or sterilized water. In a specific embodiment, the bladder is a tough, silicone material that can be filled with an appropriate liquid, semi-liquid, or gel material. In more specific embodiment, the bladder is made of a silicone elastomer that is designed for durability. This specific embodiment can have a thicker outer shell and a silicone barrier material covering the entire surface. The thicker outer shell can enable the bladder to withstand excessive or above-normal forces without failure.

In another embodiment, the bladder is flexible, but has minimal elasticity and is resistant to puncturing or tearing. With this embodiment, the bladder can react to forces by adjusting its shape to allow fluid within the balloon to be redistributed as forces are absorbed. However, the minimal elasticity of the material of the bladder can ensure that the liquid or semi-liquid material therein is redistributed within the balloon to absorb and redistribute forces, rather than causing an expansion of the bladder material itself.

In an alternative embodiment, the bladder comprises a sturdy, flexible or elastic material, such as, for example, corrugated materials, woven fiber materials, and elastic materials, or other non-homogeneous materials. In a particular embodiment, the bladder comprises a woven, flexible fiber embedded in a strong, flexible silicone elastomer. This embodiment of an embedded fiber weave can assist in maintaining the shape of the bladder when forces are exerted thereon. To further facilitate the bladder's resistance to lateral or rotational forces, the weave direction of the embedded fibers can be diagonal or cross-woven relative to the central axis CA of the force distribution boot. This can also assist is preventing unscrewing of the hydraulic dashpot from the subperiosteal strut.

In a further embodiment, the corrugated material or other bladder material can have an asymmetric thickness. For example, less elastomer and more reinforcing fiber can be utilized in one area of the bladder than in another. By way of non-limiting example, the posterior portion can have less reinforcing fiber and more elastomer material and the anterior portion can have more reinforcing material and less elastomer, making the anterior portion less flexible and the posterior portion more flexible. Similar techniques can be utilized with other materials utilized for the bladder. This configuration can be advantageous for patients wherein the applied forces are inconsistent or uneven. As forces are applied, the bladder can flex more in the posterior portion, but will expand less, and the anterior portion can expand more, but will have less flexibility.

In another embodiment, the bladder is a solid material that has sufficient elastic properties to absorb applied forces. In one embodiment, the bladder is a homogeneous material that can be compressed and deformed as forces are applied. This can include, by way of non-limiting examples, rubber, silicone, semi-solid gel matrix, foam, or similar materials. Alternatively, the bladder can be solid, non-homogenous material comprising two or more materials. The combined materials can provide elastic properties for absorbing applied forces.

In a further alternative embodiment, the bladder can be a solid of varying density that can have different compressible, non-compressible and elastic properties at different areas. Thus, the bladder can provide increasing resistance as forces applied to the bladder increase. In one embodiment, the bladder is a homogeneous material that exhibits gradual, increasing density towards the center. This, there can be an elastic, deformable surface, but an increasingly less elastic and less deformable central core. In an alternative embodiment, the bladder is a non-homogeneous solid comprised of two or more materials. In a further embodiment, the bladder comprises an external material that can provide resistance to normal forces and internal material that provides greater resistance to more extreme forces applied to the bladder. Further alternative embodiments can include successive layers of increasingly resistant materials.

In a yet further alternative embodiment the bladder can be a combination of the filled balloon like structure and the solid or semi-solid/variable density embodiments described above. With this embodiment a solid or semi solid/variable density component can be attached to the strut receiver. A balloon like structure can then be attached to the solid or semi-solid/variable density component to form a bladder that more closely mimics the hydraulic function of a natural joint.

To complete the assembly of a hydraulic dashpot, the bladder 230 is attached to a strut receiver 210. By way of non-limiting example, the bladder can include one or more structures, such as, but not limited to, flanges, tabs, hooks, or the like that allow it to be attached to various points on the strut receiver. In one embodiment, an example of which is shown on FIG. 12, the bladder includes multiple attachment tabs 235 that are contiguous with and extend therefrom that can be attached to the sides of a strut receiver.

In an alternative embodiment, the bladder can be attached directly to a strut receiver, such as by various adhesives, heat or cold sealing techniques. FIG. 5 illustrates an example of a bladder that has been adhesively attached around a strut receiver.

In a still further alternative embodiment, the bladder can be attached to a strut receiver with a clamping ring. In this embodiment, the bladder can be wrapped around the strut receiver. In a further embodiment, that part of the bladder that wraps around a strut receiver has a smaller diameter than a strut receiver, so that it can stretch and be fit over the strut receiver. In a further embodiment, the position of the bladder can be maintained with the use of one or more clamping rings 237 (FIG. 11) which are positioned over some portion of the bladder and securely clamps the bladder to the strut mechanism. In a still further embodiment, a strut receiver can have one or more grooves 238 into which the one or more clamping rings can fit to more securely hold the bladder against the strut receiver.

The attachment of the bladder to a strut receiver 210 can be achieved by any of a variety of techniques and devices. It would be well within the skill of a person trained in the art, having benefit of the subject disclosure, to determine any of a number of techniques and devices that could be used to permanently or removably attach a bladder to a strut receiver. In either case, it should provide a biocompatible, secure attachment that allows the strut receiver and bladder to operate as necessary. It should be understood, therefore, that such variations in the attachment means are considered to be within the scope of the subject invention.

The factors that can be considered by those skilled in the art with regard to the choice of materials for the components of the subject invention have been discussed above and are reasserted here with regard to the hydraulic dashpot and the components thereof. Such material modifications to the hydraulic dashpot, as would be apparent to a person skilled in the art having benefit of the subject disclosure, are deemed to be within the scope of the present invention.

II. Methods and Devices for an Intermittent and/or Variable Electromagnetically Controlled Prosthetic System:

Once the residual limb has been prepared, a prosthetic device 20 can be attached to the end of the residual limb. The attaching and securing of a prosthetic device can be accomplished in several ways. Typically, a variety of belts, bands, straps, cuffs, harnesses, sockets, suction sleeves and the like are used to secure a prosthesis against a residual limb. It is important that the prosthesis be attached securely, so there is sufficient control of the prosthesis and ease and range of movement. Further, if the prosthesis is not secure against the residual limb it can cause chafing or abrading of the skin, which can lead to other complications. Unfortunately, with most devices, securing the prosthesis well enough to prevent undesirable movement, often results in impaired circulation, i.e., ischemia, in the limb. Over time, continued ischemia can cause pain in the residual limb and, in extreme cases, tissue degradation.

Other methods utilize skeletal extensions, such as rods or various mechanisms that protrude from the body. The advantage to these devices is that the prosthesis is attached to the extension and pressure is exerted directly on the bone. This reduces stress on the tissues and often provides very secure attachment of the prosthesis. The disadvantage with most of these systems, however, is that the tissue around the extension exit area may not heal properly or can leave a sinus or other wound opening that is susceptible to infections and other complications.

Embodiments of the subject invention include an intermittent and/or variably controlled electromagnetic attachment system, whereby the above-described implantable force distribution boot 10 includes components that allow it to be magnetically attached to an external prosthesis. Additional embodiments reduce ischemia in the tissues and increase the comfort of the patient. These embodiments can also be utilized with an improved surgical technique for preparing the residual limb, which will also be discussed below.

A typical electromagnetic system includes an electromagnet and an armature plate. In most applications of an electromagnetic system, the electromagnet is attached to one device and the armature plate to another device. A current passing through the electromagnet causes it to be attracted to the armature plate, which can hold the two devices together. Thus, as long as there is an electric current passing through the electromagnet, the two devices can be maintained in a predetermined position. Also, by adjusting the amount of electrical current, the force of attraction between the electromagnet and the armature plate can be controlled.

Figure 6:
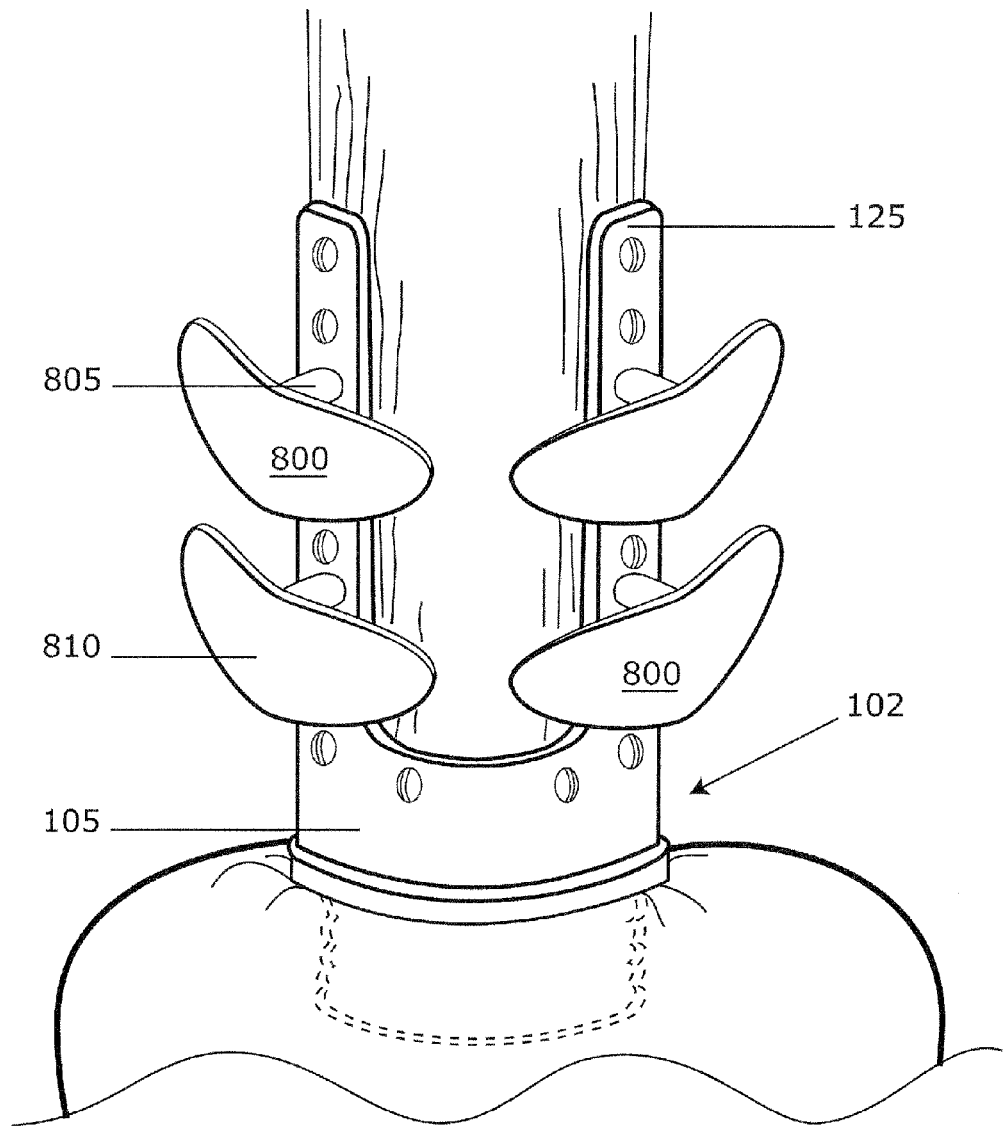
FIG. 6 shows a perspective view of an alternative embodiment of the modular, implantable force-distribution boot, wherein the blades are horizontally aligned.

In one embodiment, a subperiosteal strut 100 includes one or more blades 800, as shown, for example, in FIGS. 2, 6 and 8. A blade can act as a specialized, implanted armature plate that can be used in conjunction with an electromagnet associated with an external prosthesis. When the electromagnet is activated by electric current, it is attracted to the one or more blades on the implanted subperiosteal strut. This attractive force holds the prosthesis against the residual limb.

In a further embodiment, a blade is a structure made of one or more biologically compatible magnetically attractable materials. In a still further embodiment, a blade can be covered or sealed in one or more biologically compatible materials that do not affect the overall magnetic properties of the blade. In a more specific embodiment, a blade is a biologically compatible ferromagnetic material to which an electromagnet can be attracted. Iron, nickel, and cobalt are non-limiting examples of ferromagnetic materials that can be utilized with the embodiments of the subject invention. Other natural or man-made materials could also be utilized. A person with skill in the art would be able to determine appropriate materials, ferromagnetic or otherwise, that would be suitable for a blade according to the embodiments of the subject invention. Such variations are contemplated to be within the scope of the subject invention.

In one embodiment, a blade 800 is attached directly to a subperiosteal strut. In a more particular embodiment, a blade is attached directly to a stanchion 125 that can be, or is, part of a subperiosteal strut. In some cases, as discussed above, it can be advantageous for a blade to be permanently attached to a subperiosteal strut and/or a stanchion. In other cases, it can be preferable for a blade to be removably attached, which allows for alteration or replacement if necessary.

Figure 3:
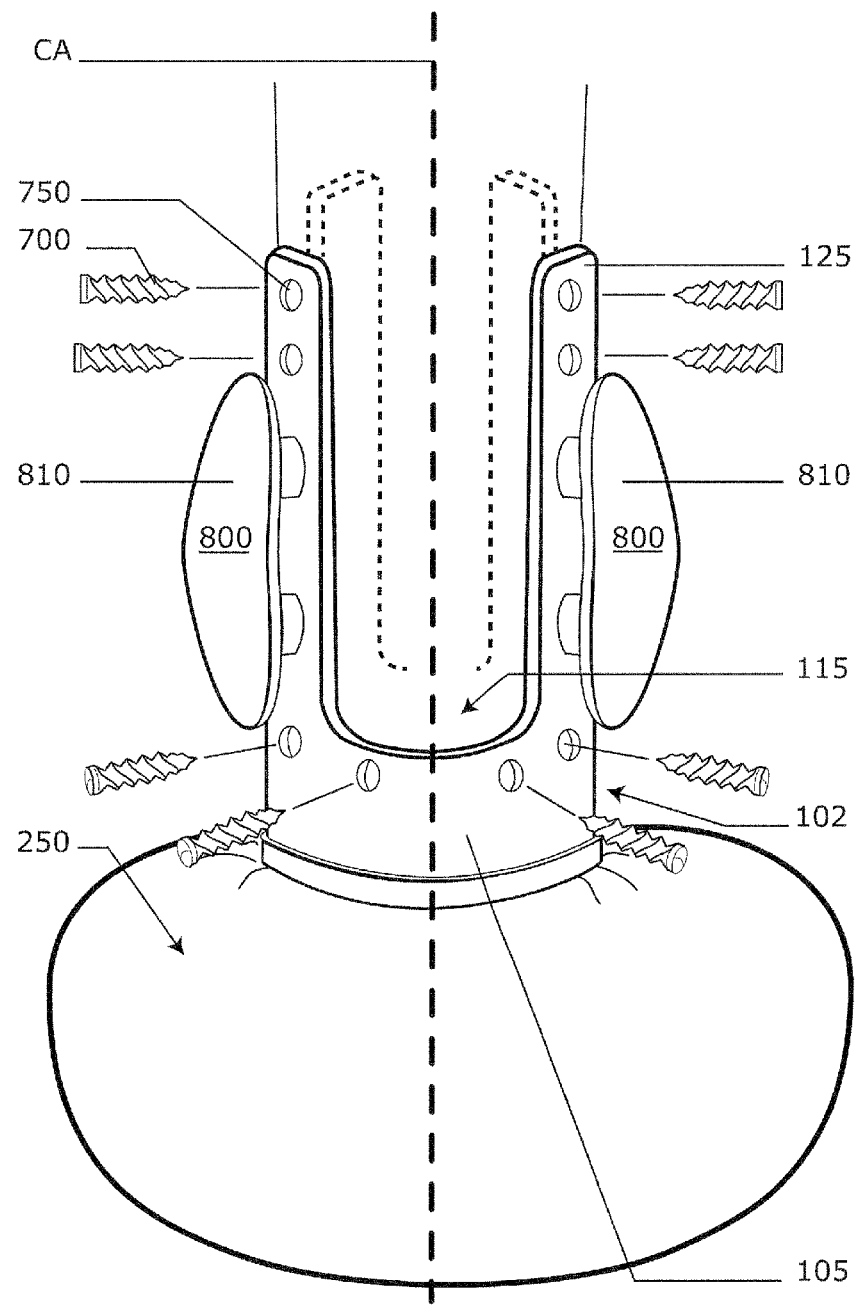
FIG. 3 is an enlarged perspective view of an embodiment of the force-distribution boot installed on the femur bone of an above-knee-amputation (AKA), indicating one optional placement of the anchoring screws.

In an alternative embodiment, a blade 800 is attached to a post 805, which is removably or permanently attached to a subperiosteal strut and/or a stanchion. In a further embodiment, a blade is attached to more than one post. FIGS. 3, 6, and 9A show examples of an embodiment where a blade is affixed to a stanchion using two posts.

Since the blades will be implanted into the residual limb, the shape of a blade should be such that it is compatible with the normal shape of the residual limb, and should be comfortable and compatible with the internal tissues. Ideally, the shape of a blade is curved to match the shape of the residual limb and is generally smooth, particularly on the front surface 810. In a more specific embodiment, the front surface 810 is a convex shape. FIG. 6 illustrates an example of an embodiment where the blades are elongated with a horizontally-aligned curvilinear shape. FIG. 9A illustrates an example of an embodiment where the blades are elongated with a vertically-aligned curvilinear shape. Other embodiments include blades that are aligned to one or more angles. Since the purpose of the one or more blades is to be attracted to one or more electromagnets 815 on or within the prosthesis, it can be beneficial if the blades are aligned appropriately, at whatever angle, to operably and comfortably connect with the electromagnets. Variations in the angle of a blade are considered to be within the scope of the subject invention.

Figure 16:
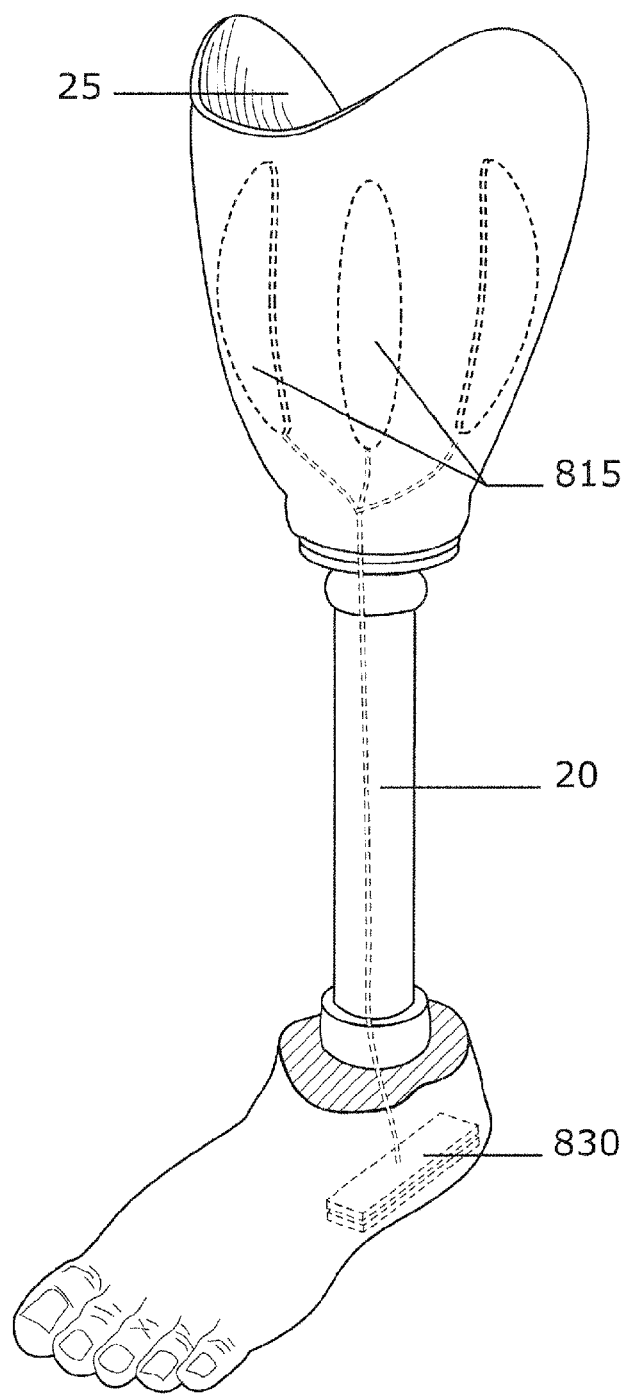
FIG. 16 is a left side perspective view of one embodiment of a prosthetic device with multiple electromagnets within the socket well. In this embodiment, the electromagnets are controlled by a switch in the foot of the prosthesis that is wired to the electromagnets.
Figure 17:
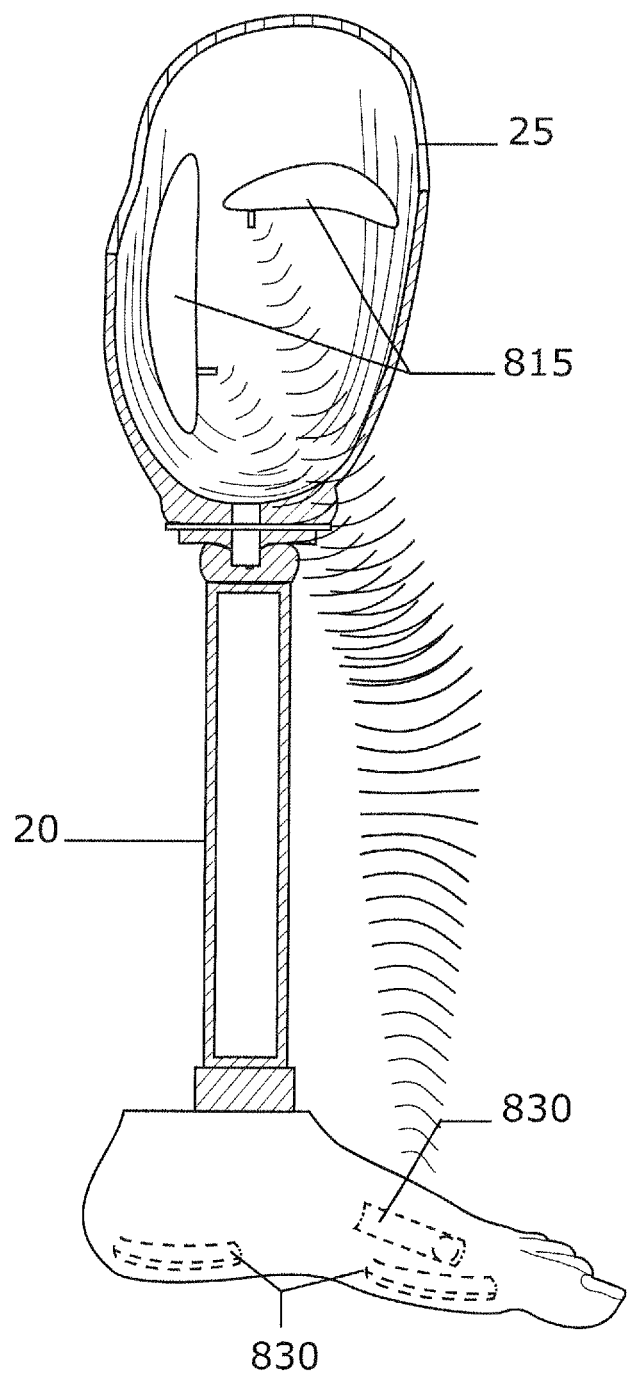
FIG. 17 is a cross-sectional, right side elevational view of an embodiment of a prosthetic device showing alternative positions of electromagnets within the socket well. This embodiment is an example of a switch that controls the electromagnets remotely, such as, for example, by radio or sound waves.
Figure 18:
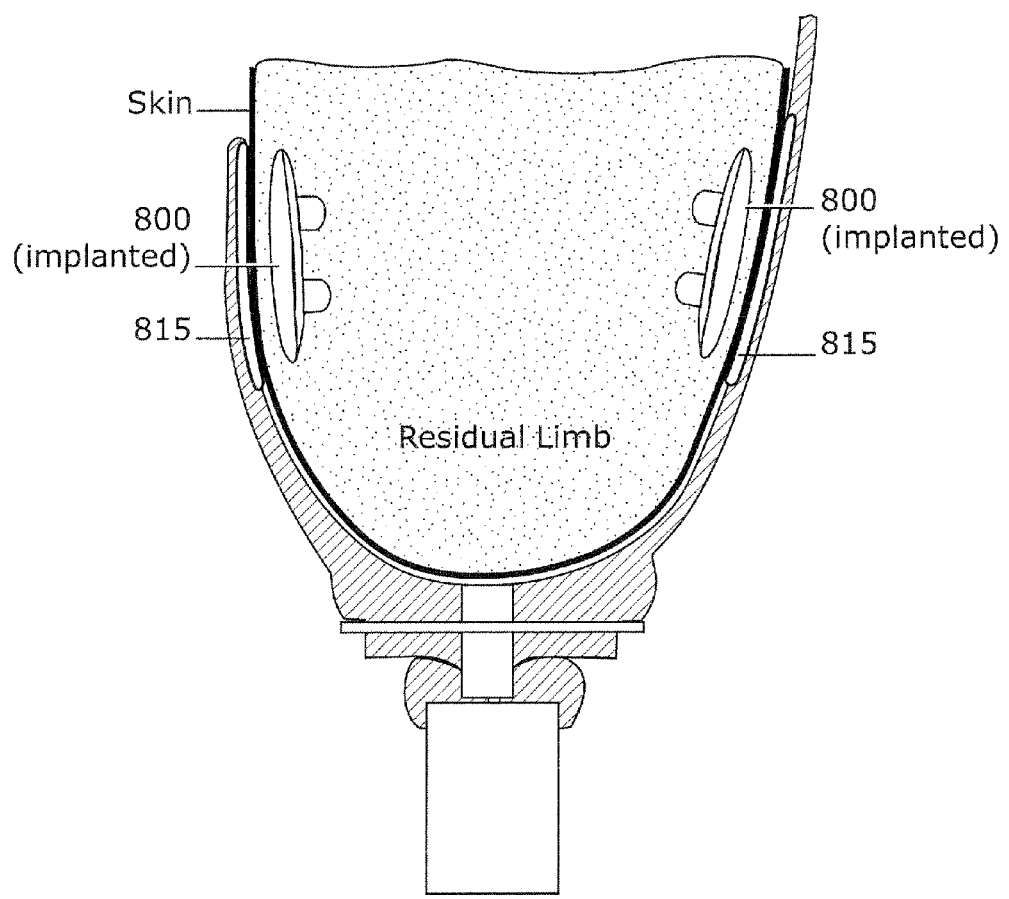
FIG. 18 is a cross-section, front elevational view of a socket well with an inserted residual limb, showing how the blades operably connect to the electromagnets.
Figure 19:
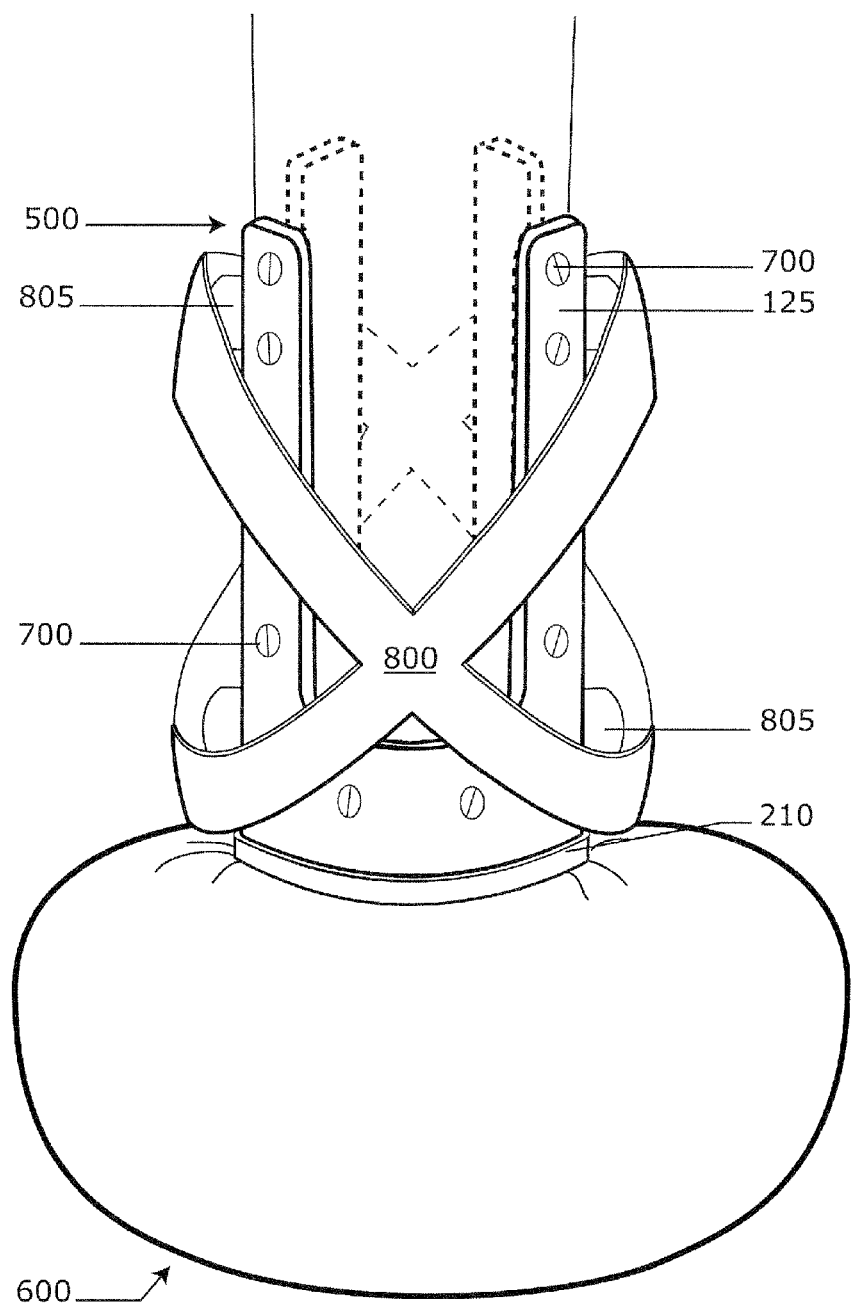
FIG. 19 is an illustration of an alternative embodiment or the subject invention having two blades that curve around the stanchions and overlap at an angle with each other.
Figure 20:
FIG. 20 is a photograph showing an example of a plantar surface that can be harvested utilizing the surgical methods disclosed herein.
Figure 21:
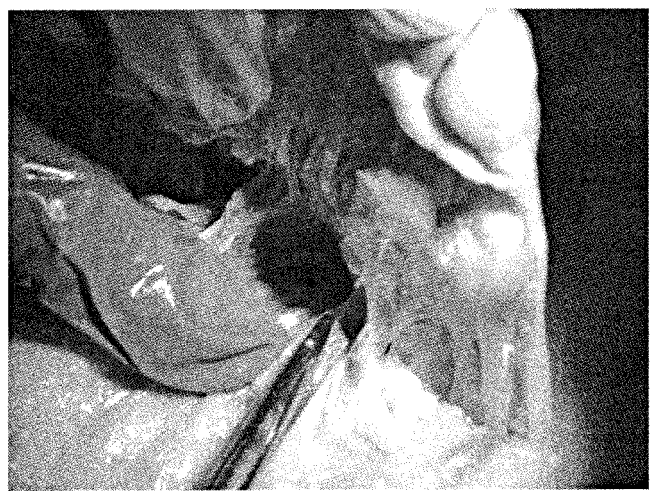
FIG. 21 is a photograph showing an example of the dissection plane and demonstrating cut long and short plantar flexor tendons with transition into deep plantar space that provides an avascular plane to the calcaneus. This space can allow for the reflection of the plantar myocutaneous flap inferiorly and can provide an approach and subperiosteal removal of the calcaneus tissue. The only arterial ligation typically needed is the communicating artery that joins the plantar arch.
Figure 22:
FIG. 22 is a photograph showing a plantar myocutaneous flap based on posterior tibial artery (PTA) with short and long flexor tendons reflected inferiorly protecting the distal branches of the PTA. This approach can allow for release of the tendonus origin of the Quadratus and Flexor Digitorum Brevis muscles and quick access to the calcaneus subperiosteal plan. This can also ensure preservation of the internal and external Calcanean Anastomosis.
Figure 23:
FIG. 23 is a photograph showing an example of a plantar myocutaneous flap reflected inferior-posterior demonstrating remaining interosseous, adductor, abductor muscles and deep long plantar ligament of foot, as well as calcaneus after subperiosteal dissection of the flap. The hemostat in the photograph points to the neurovascular pedicle with remaining soft tissue investments. Note cut long flexor tendons.

In a further embodiment, a prosthesis 20 is configured with one or more electromagnets, 815 that are on or within, ("onboard") the prosthesis, can be activated to be attracted to the implanted blades. FIG. 16 illustrates an embodiment of a prosthetic device 20 fitted with multiple electromagnets 815. To enhance the connectivity between a blade and an electromagnet, it can advantageous for the electromagnets to reside within or otherwise be associated with that part of the prosthesis that would be closest to the blades implanted within the residual limb. FIG. 17 illustrates an embodiment where the electromagnets are located within, or are part of, a socket well 25 of a prosthetic device 20. The power source for the electromagnet can be incorporated as part of the prosthesis and can be operably connected by any of a variety of techniques or devices known in the art. Alternatively, the power source could be separate from the prosthesis. It would be well within the skill of a person trained in the art to determine any of a variety of techniques and devices for providing power to the one or more electromagnets incorporated into a prosthesis. Such variations are considered to be within the scope of the subject invention.

In a particular embodiment, the electromagnets have a shape that is compatible with the shape of the blades, such that when the blades and the electromagnets come together, the tissue therebetween is not pinched, cut or otherwise hurt. In one embodiment, the electromagnets have a slightly concave shape into which the curvilinear shape of a blade can be fit. FIG. 17 illustrates two embodiments wherein the electromagnets are vertically-aligned and/or horizontally-aligned to fit with vertically-aligned or horizontally-aligned blades. As discussed above, the alignment of the electromagnets can vary and it can be most beneficial if the electromagnets are aligned appropriately, at whatever angle, to operably and comfortably connect with the implanted blades. Such variations are contemplated to be within the scope of the subject invention.

It can be important to ensure that circulation within the residual limb tissues is not constricted, to prevent ischemia. To prevent tissue between the blades and the electromagnets from becoming ischemic, the force between a blade and an electromagnet can be released or lessened periodically to encourage circulation. However, releasing or lessening the magnetic force can cause the prosthesis to disengage from the residual limb. To prevent the prosthesis from disengaging, it can be advantageous if the force was released or lessened only when other forces, such as gravity, are able to maintain the position of the prosthesis.

In one embodiment, one or more sensors 830, operably connected to the electromagnets, can detect when the prosthesis is in a position where the magnetic force between a blade and an electromagnet can be released without risk of the prosthesis being disengaged from the residual limb. In a particular embodiment, the sensor is a motion- or gravity-activated device, such as, by way of non-limiting examples, a ball-bearing switch, mercury switch, weighted trip-switch and the like operably attached to the electromagnet. In an alternative embodiment, the sensor is a motion or proximity activated relay or switch such as, for example, laser activated, infrared activated, radio-wave activated or acoustically activated switches. In a still further alternative embodiment, the sensor is a pressure-activated device, such as, by way of non-limiting examples, a push-button, pressure-pad, spring-button, and the like operably attached to the electromagnet. When a sensor is in the "on" or activated position, the electromagnetic forces are in operation. Likewise, when the sensor is in the "off" or deactivated position, the electromagnetic forces cease. Thus, an appropriately placed sensor or sensors could detect signals received during walking or other ambulation and the magnetic forces can cycle on and off, independently, in groups, or all together, depending upon the position of the prosthesis, or even the opposite leg. A person with skill in the art, having benefit of the subject disclosure, would be able to determine the appropriate placement of a sensor or sensors that can detect specific signals generated by ambulation or other motion to control the electromagnetic forces.

In one embodiment, one or more sensors 830 can be positioned on or within, ("on-board"), the prosthetic device, so that when the prosthetic device is aligned, such that gravity will hold the prosthesis in place against the residual limb, the sensor can cease, or reduce, the flow of electric current. When the electric current is reduced or is no longer coursing through the electromagnet at all, the attraction between the blade and the electromagnet is also reduced or ceases entirely, reducing or eliminating pressure on the tissues therebetween, allowing circulation. It can be advantageous if the sensor and/or electromagnet have the ability to be activated and deactivated quickly, so that motion is not restricted due to a delayed response.

In another embodiment, a prosthetic device is configured with an appropriate sensor that can be activated and deactivated during normal walking motions. With this embodiment, when the prosthetic device is sufficiently vertically-aligned and the foot is against the ground or other surface, the residual limb can rest within and against the bottom of the socket well 25. In this position, gravity can be the sole force holding the prosthesis against the residual limb. The sensor can, therefore, be activated, by whatever means dictated, to turn off the electromagnet and allow perfusion of the tissues. When the sensor detects a change in the position of the prosthesis, or some part thereof, such as, for example, when the patient resumes or continues the walking motion, when some portion of the prosthetic foot is no longer against the surface, when the opposite leg changes position, when the prosthetic device is no longer vertically-aligned, or when some other pre-defined event occurs, the sensor can immediately detect the change in position and quickly activate the electric current to reactivate the electromagnets. Thus, during normal walking motion, an electromagnet could cycle through being turned on and off multiple times, reducing or eliminating ischemia of the tissues.

In an alternative embodiment, the electromagnetic forces are applied in variable strength or intermittently to adjust or adapt to the forces and pressures of walking. In a further embodiment, one or more on-board sensors are utilized with the prosthesis that can sense when the prosthesis is in, or is about to be in, a position where gravity can maintain the position of the prosthesis against the limb. With this embodiment, when the foot portion of the prosthesis approaches a surface, the sensor or sensors, such as, for example, a laser-light sensor or radio-wave sensor, will detect the approaching proximity of the surface and can gradually reduce the electrical current through the electromagnet. This allows tissue perfusion to begin. When the foot portion is securely against the ground, the electromagnetic forces can be completely off or sufficiently reduced so that full tissue perfusion can occur. As the walking motion continues, the sensor detects a change in position, such as, for example, the foot being raised from the surface, and the electromagnetic forces are gradually reapplied to ensure that the prosthesis stays firmly attached to the residue limb.

In a further alternative embodiment, the electromagnets can be paired or grouped, so that they cycle through the above-described process in a rotational fashion. By way of non-limiting example, a prosthesis can be configured with two or more groups of electromagnets controlled by one or more sensors. During the walking motion, when the sensors detect the various changes described above, each group of electromagnets can be activated or deactivated at opposite times. Thus, during one cycle a first group of electromagnets will remain at full strength, while a second set of electromagnets will be reduced in strength or turned off, allowing tissue perfusion in that area to occur. During the next cycle, the first group of electromagnets will be reduced in strength or turned off, allowing tissue perfusion in those areas, while the second set will remain at full strength. The advantage to this arrangement is that the prosthesis is always secured to the residual limb, independent of gravity or other external forces, but tissue perfusion is still possible. It is not uncommon for prosthetic devices to include various switches, controls or manually operated mechanisms to manipulate the prosthetic device in different situations, such as standing, leaning or sitting. By way of non-limiting example, a manual on/off switch for the electromagnets, knee-locking and unlocking mechanisms (e.g., bail-locks, Swiss locks, or French locks), and other devices can be utilized with the embodiments of the subject invention. It is contemplated that the addition of such devices, where they do not significantly alter the function of the embodiments described herein, are within the scope of the subject invention.

III. Surgical Method for Harvesting and Implanting Glabrous Tissue:

One of the most difficult problems that a lower extremity amputee patient can face is being able to transition to the use of a new prosthesis. In some cases, patients may take years to fully adapt to a prosthesis. This delay in the use of the prosthesis is often due to the physiological changes that occur in the extremity during healing and afterwards during normal daily activities. This transition to use is further complicated by the skin and the boney prominences of the residual limb preventing comfortable and consistent use of the prosthesis. This is usually because the skin covering the amputation is not physiologically or anatomically suited for the pressures involved in walking. As a result, 25% of patients experience ulcerations and delayed wound healing from this physiological mechanical skin mismatch on the residual limb. Use of a prosthesis can be further limited by pain and discomfort it causes in the limb. Amputees receive on average a new prosthesis every two years.[3]

These problems can be further complicated by marked variation in the surgical amputation techniques and socket manufacturing processes, both of which are performed by skilled artisans. But, regardless of how advanced the prosthesis may be, if the amputee cannot use it because the residual limb is prepared anatomically and physiologically incorrectly, then it is worthless. For these reasons, it seems evident that attempts to reconstruct or transplant the evolutionary adapted weight bearing and friction tolerating glabrous skin of the foot to the amputee stump would help prevent these complications.

The successful use of vascularized plantar glabrous skin free flaps from the sole of the foot in reconstruction of like skinned areas is known in the art, including its use on a BKA.[4,5,6] The success of this technique has been achieved because the vascular anatomy of the foot and its plantar surface has been well documented through dissection and angiographic studies.[7,8,9,10,11] These studies have demonstrated that the glabrous skin and deep muscles of the plantar surface of the foot receive their blood supply from the Posterior Tibial Artery (PTA) and its distal divisions—the medial and lateral plantar, plantar arch and metatarsal branches. The PTA also supplies the medial calcaneus region and has lateral anastomatic connections with the External Calcanean, the terminal branches of the Posterior Peroneal Artery (PPA) through the PTA's Internal Calcanean branches. Distally the Communicating Artery from the Dorsalis Pedis Artery passes between the first two heads of the Dorsal Interosseous Muscle then joining with the Plantar Arch. This artery is typically ligated as it is encountered during the development of the plantar flap, just proximal and between the first and second metacarpal-phalangeal joints. The embodiments disclosed herein demonstrate a feasible Myocutaneous Flap that can be developed using the knowledge of this anatomy.

The surgical technique of implanting vascularized plantar glabrous skin free flaps can improve the surgical management of traumatic or elective lower extremity amputations with the goal of preparing an amputee residual limb that is better suited for weight bearing and the activities of daily life. More specifically, the surgical techniques described herein allow for harvesting of myocutaneous flaps that are different from the traditional amputation flap designs used today (such as skew, sagittal, or long posterior flaps), and provide a Plantar Myocutaneous Free Flap that can be inset within a residual limb terminal end for maximum efficiency and coverage. When utilized in conjunction with embodiments of the herein described implantable prosthetic device, external prostheses can be used with less discomfort and few complications.

In one embodiment, the force distribution boot described herein is utilized with the surgical technique of implanting vascularized plantar glabrous skin free flaps over the terminal end of a residual limb. In a further embodiment, the electromagnetically controlled prosthetic device described herein is utilized with a residual limb that has been prepared by implantation of a vascularized plantar glabrous skin free flap. The utilization of a vascularized plantar glabrous skin free flap can improve the successful use of the force distribution boot and the accompanying electromagnetically controlled external prosthesis.

The embodiments disclosed herein were perfected through cadaver dissections of lower extremities, which assisted in the development of an efficient and rapid Plantar Surface Myocutaneous Free Flap harvest technique. The cadaver dissections were performed in the Psychomotor Surgical Skills Laboratory at the University of Florida, Department of Orthopedics Orthopedic and Rehabilitation Institute in Gainesville, Fla. One complete hip disarticulated extremity and two below the knee disarticulated extremities were used to develop the three flaps. These same specimens were used to create two BKAs and one AKA that the improved plantar flaps were inset on. Standard surgical instruments, sutures and techniques were used to design, dissect and remove the plantar flaps. Therefore, the embodiment disclosed herein will be described with regard to the faux vascular and neuroraphy procedures as performed on cadaverous tissue. It is anticipated these techniques and procedures would be directly applicable to a patient.

A. Method for Obtaining Vascularized Plantar Free Flaps (VPFF):

Partial lower extremity cadaver legs were used for development of VPFF and creation of BKA or AKA amputations. Dissection of the VPFF was then undertaken on three separate lower extremities as outlined below.

First, the VPFF area to be harvested can be outlined with a standard marking pen. This area can include all the skin of the plantar surface using the lateral-anterior surface of the metatarsals of the great toe and little toe as the lateral edges of the flap.

The line of dissection can then continue anterio-plantar to include the plantar tissue just beyond the metatarsal-phalange joint of the plantar surface, joining the medial and lateral lines of dissection.

The line of dissection can be carried posterior just inferior to the medial and lateral malleolus of the ankle and joined posterior at the Achilles tendon above its calcaneus insertion and just inferior to the medial and lateral malleolus.

The approach to the Posterior Tibial Artery (PTA) can be outlined using a marking pen to demonstrate the medial line of the anterior surface of the tibia.

There are two routes of dissection for exposure of the PTA that can be used.

The first route involves exposure of the PTA by incising the skin just medial to the medial edge of the tibia and identifying the Greater Saphenous Vein (GSV) which was preserved and harvested. The plane between the Flexor Digitorum Longus inferior and the Soleus superior can then be identified and using this fascial plane, the posterior neurovascular compartment can be entered, exposing the PTA, veins and nerve.

The PTA and Posterior Tibial Nerve (PTN) can then be used as the plane of dissection, carrying the dissection distally behind the medial malleolus of the ankle. The PTA, PTN and the venea comitantes can be reflected posterior with the developing flap.

The entire plantar surface of the foot can then be dissected free by incising through the skin into and below the periosteum of the medial and lateral metatarsals, incising the superficial and deep plantar flexors (Flexor Digitorum Longus and Brevis, Lumbricals, and Flexor Hallucis Longus and Brevis) into the periosteum. The dissection can then be carried along the periosteum and the plane of dissection transitioned into the deep plantar space. This space creates a natural plane of dissection from which to harvest the fully vascularized plantar myocutaneous free flap. Continuing, the dorsal perforating artery can be ligated proximal to the greater metatarsal-phalange joint as it penetrates dorsally. The flap is developed proximal towards the calcaneus. The short flexors are carried with the flap taking the Quadratus Plantae with the flap, but leaving the lumbricals, interosseous, abductors muscles and the long plantar ligament in place. At this point, the PTA is superficial to this plane of dissection and its passage between the Quadratus and the Flexor Digitorum Brevis.

Using the deep plantar compartment, the dissection can be carried to and below the periosteum of the calcaneus, using this plane to free the flap from the calcaneus.

The skin can be incised over the Achilles tendon and the tendon bisected. The dissection is then carried deep medial and lateral down to and including the ankle's ligamentous capsule. Ideally, this keeps the vascular pedicle safely reflected away. All flexor tendons can then be cut as they rotate behind the ankle into the plantar surface of the foot, protecting the Neurovascular pedicle during these divisions.

The dissection can then be carried over to and below the periosteum of the calcaneus where the insertion of the Achilles tendon is then freed and the flap is left tethered to the neurovascular pedicle.

Preferably, the posterior peroneal artery is not dissected although identified laterally ligated at its termination of the external calcanean, which communicates with the internal calcanean of the PTA. (FIGS. 20-23)

Utilizing this method, two free microvascular plantar tissue grafts can be dissected free, with little risk to the vascular pedicle, since it is deep to all planes of dissection. The pedicle may be at some risk when freeing the neurovascular pedicle as it passes posterior and deep to the medial malleolus. This free flap can be de-bulked, if desired, of flexor tendons and excess muscle if done carefully without injuring the vascular pedicel distribution. A flap not dissected with this method was a subcutaneous supra-muscular plantar dissection that lacked significant bulk and fibrous tissue such as calcaneus periosteum and flexor tendons and muscles.

Figure 24:
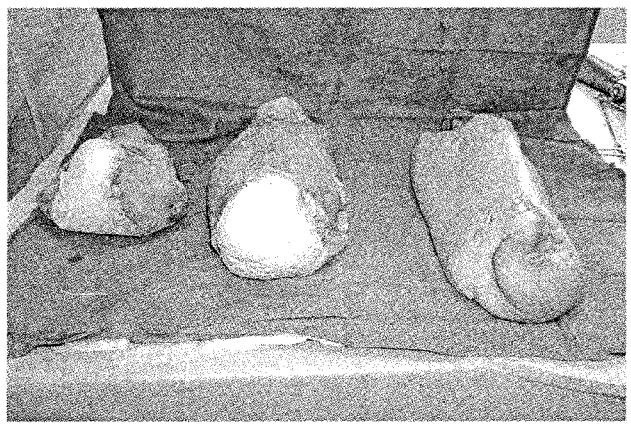
FIG. 24 is a photograph showing three examples of vascularized plantar free flaps (VPFF) inset into BKA and AKA stumps Left to Right - proximal BKA, distal BKA and distal AKA Plantar heel superior.
Figure 25:
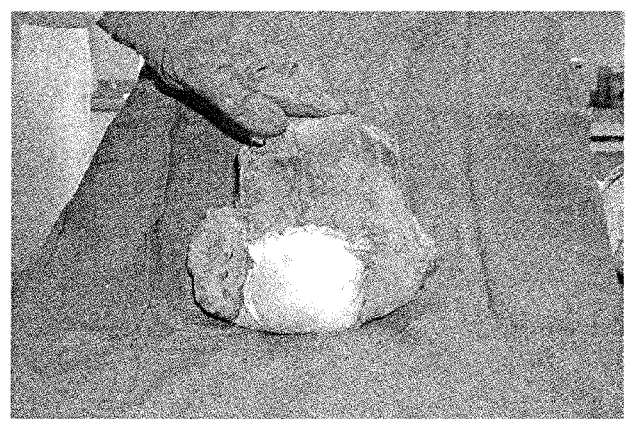
FIG. 25 is a photograph showing an example of a proximal tibial amputation with posterior long flap VPFF inset with plantar heel anterior Long flap bisected and trimmed to allow flap inset (not recommended flap).
Figure 26:
FIG. 26 is a photograph showing an example of a lateral view of distal tibial BKA with VPFF inset with modified fish mouth or bivalve flap. In this example, the plantar heel is anterior (Right) with distal plantar skin posterior (Left). Flap provides for anterior skin protection from boney prominence of anterior tibia and glabrous surface for weight bearing in future prosthetic socket pressure.
Figure 27:
FIG. 27 is a photograph showing an example of a fish mouth or bivalve amputation flap for distal AKA.
Figure 28:
FIG. 28 is a photograph showing an example of a distal fish mouth or bivalve AKA flap and an exposed PTA with dissected plantar flap.
Figure 29:
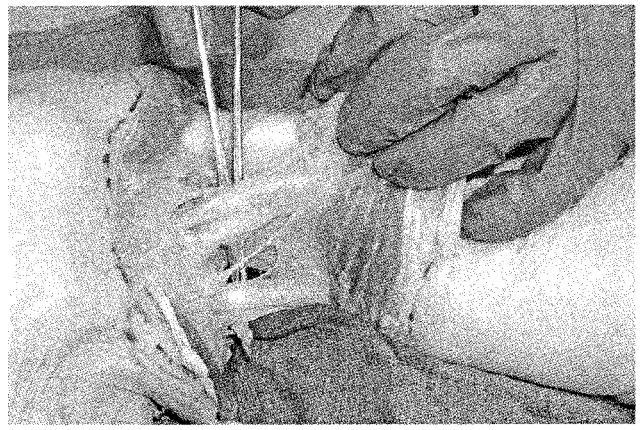
FIG. 29 is a photograph showing an example of an AKA Popliteal vein, artery and tibial nerve—superior to inferior.
Figure 30:
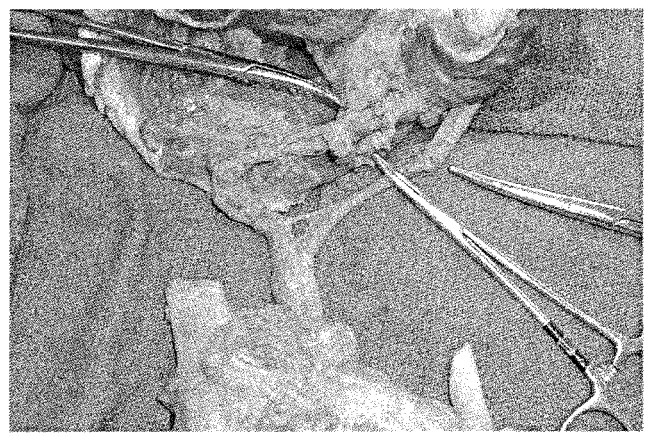
FIG. 30 is a photograph showing an example of a Faux neuroraphy End-to-End (scissors) Faux arterial and venous end-to-side anastomosis (hemostat). It is suggested that identification and preservation of Greater Saphenous Vein be done, so that it can be used as intermediate reducing conduit from femoral artery to PTA for end-to-end anastomosis.
Figure 31:
FIG. 31 is a photograph showing a lateral view of an example of an AKA with VPFF inset into fish mouth or bivalve AKA flap. In this example, the plantar heel is superior (indicated by the clamp) and distal plantar skin is posterior (indicated by the scissors). VPFF provides excellent coverage for future prosthetic socket weight bearing area.

Two standard surgical proximal and distal BKAs were created on two separate cadaver legs, with a long posterior flap (that would have traditionally covered the Tibial boney stump). The proximal PTA and Anterior Tibial Artery (ATA) can be also indentified for possible anastomatic vessels along with the PTN. A VPFF can be placed over the exposed surface of the BKA stumps with the neurovascular pedicle matched to its corresponding proximal counterpart with a microvascular anastomosis and tibial nerve neuroraphy completed. The neurovascular pedicle can be positioned to prevent pressure on it that could compromise blood flow during healing. The flaps can then be sutured into position by placing the heel tissue anteriorly and distal plantar skin tissue posteriorly. The long posterior flap can then be modified. Preferably, the thickest plantar skin is positioned over the anterior boney prominences. FIGS. 24-26

In a further example, an AKA was created on another cadaver leg using a lateral fish mouth flap and the femoral bone cut proximal at the angle of fish mouth flap. The femoral boney stump was covered with the VPFF after the neurovascular attachments were completed. As in the BKA flap placement the heel tissue of the VPFF was place anteriorly and distal plantar skin tissue was placed posteriorly with the pedicle carefully protected deep, as the wound was closed. (FIGS. 23, 27, 28, and 29)

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited herein are also entirely incorporated by reference.

It should be understood that the examples and embodiments described herein are for illustrative purposes only and that various modifications or changes in light thereof will be suggested to persons skilled in the art and are to be included within the spirit and purview of this application.

It should be understood that any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself. Further, it should be understood that, although the present invention has been described with reference to specific details of certain embodiments thereof and by examples disclosed herein, it is not intended that such details should be regarded as limitations upon the scope of the invention except as and to the extent that they are included in the accompanying claims.

CITED REFERENCES

1—Amputations in US Military Personnel in the Current Conflicts in Afghanistan and Iraq; Stansbury, LG; Lalliss, CJ; Branstetter, JG, Bagg, MR; Holcomb, JB; *Journal of Orthopedic Trauma*; Vol 22, No. 1; 2008; pp 43-46

2—Amputation Statistics by Cause: Limb Loss in the United States; NLLIC Staff; National Limb Loss Information Center; revised 2008; http://www.amputee-coalition.org/fact_sheets/amp_stats_cause.pdf; accessed May 3, 2011

3—Use and Satisfaction with Prosthetic Devices Among Persons with Trauma-Related Amputations: A Long-term Outcome Study; Dillingham, TR, M.D.; Pezzin, LE, Ph.D.; MacKenize, EJ, Ph.D.; Burgess, A R, M.D.; *American Journal of Physical Medicine and Rehabilitation*; Vol. 80, No. 8, august 2001, pp 563-571

4—Comparison of Sole to Palm Reconstruction Using the Combined Medial Plantar and Medial Pedis Free Flaps and Abdominal Pedicle Flap for Extensive Palm Injuries; Masoud Yavari, Mohammad Reza Ghazisaidi, Shokufeh Hoseini Zahmatkesh, and Ramin Jahadi; *Acta Medica Iranica*, Vol. 48, No. 4 (2010); pp 214-217

5—Weight-bearing plantar reconstruction using versatile medial plantar sensate flap; Suk Joon Oha, Mincheol Moona, Jeongho Chaa, Sung Hoon Koha, Chul Hoon Chungb; *PJRAS*; Volume 64, No. 2, February 2011; pp 248-254

6—Use of an Osteocutaneous Plantar Free Flap for Salvage of a Below-the-Knee Amputation in a Child. A Case Report; Waters, P. M., M.D. and Taylor, B. A., M.D.; *The Journal of Bone and Joint Surgery* 79:1073-5 (1997)

7—*Gray's Anatomy;* Henry Gray FRS; 1901; Reprinted 1995 Barnes and Nobles; Fifteenth Edition; pp 563-570

8—Variations of the Arterial Anatomy of the Foot; Taro Yamada, M.D., Peter Gloviczki, M.D., Thomas C Bower, M.D., James M. Naessens, MPH and Stephen W. Carmichael, Ph.D; *The American Journal of Surgery*; Vol. 166; August 1993; pp 130-135

9—Anatomic Study of Blood Supply of the Dorsum of the Foot and Ankle; Teresa Vazquez, Ph.D., Marc Rodriguez-Niedenfuhr, M.D., Ian Parkin, M.D., Fermin Viejo, M.D., and Jose Sanudo, M.D.; *Arthroscopy: The Journal of Arthroscopy and Related Surgery*; Vol. 22, No. 3 (March), 2006: pp 287-290

10—Anatomical Study of Cutaneous Venous Flow of the Sole; Nobuaki Imanishi, M.D., Kazuo Kish, M.D., Hak Chang, M.D., Hideo Nakajima, M.D., Sadakazu, M.D.; *Plastic and Reconstructive Surgery*; Vol 120, No. 7, December 2007, pp 1906-1910

11—Angiosomes of the Foot and Ankle and clinical Implications for Limb Salvage: Reconstruction, Incisions and Revascularization; Christopher E. Attinger, M.D. Karen Kim Evans, M.D., Erwin Bulan, M.D., Peter Blume, D.P.M., Paul Cooper, M.D.; *Plastic and Reconstructive Surgery*; Vol 117, No. 7S, June Sup 2006, pp 261S-293S 12—Limb Salvage versus Traumatic Amputation: A Decision Based on a Seven Part Predictive Index; Russell, W. L., M.D., Sailors, D. M., M.D., Whittle, T. B., M.D., Fisher, D. F., JR., M.D., and Burns, R. P., M.D.; *Ann Surg.*; Vol. 213, No. 5, May 1991; pp 473-480

13—Estimating the Prevalence of Limb Loss in the United States: 2005 to 2050 Ziegler-Graham, K., PhD, MacKenzie, E. J., PhD, Ephraim, P. L., MPH, Travison, T. G., PhD, Brookmeyer, R., PhD; *Arch Phys Med Rehabil*; Vol 89, No. 3, March 2008; pp 422-429

I claim:

1. A modular prosthetic force distribution boot comprising:
    a subperiosteal strut having a proximal end and a distal end, where proximal end receives a residual bone end in an amputated limb, such that at least the residual bone end abuts the subperiosteal strut:
    a hydraulic dashpot comprising,
        a strut receiver that can be removably attached to the distal end of the subperiosteal strut to allow for alteration or replacement of the hydraulic dashpot; and
        a bladder fixedly attached to the strut receiver and having a portion of the bladder located distally to the strut receiver,
    wherein the force distribution boot is implantable within a residual amputated limb, such that forces exerted on or about the terminal end of the amputated limb are absorbed by and distributed internally by the portion of the bladder.

2. The modular prosthetic force distribution boot, according to claim 1, wherein the subperiosteal strut is a femoral subperiosteal strut comprising a sleeve having a proximal end and a distal end and an interior space there between, for receiving at least the residual bone end.

3. The modular prosthetic force distribution boot, according to claim 2, further comprising:
    a diaphragm disposed within the sleeve that divides the interior space into a proximal femur socket, and distal set-screw bore, where the femur socket receives at least the residual bone end, and
    a set-screw port within the diaphragm that communicates the femur socket with the set-screw bore.

4. The modular prosthetic force distribution boot, according to claim 3, further comprising a dual-end set-screw having a proximal end that can extend through the set-screw port into the femur socket and be attached to the intermedullary space of the residual bone and a distal end that engages with the set-screw bore.

5. The modular prosthetic force distribution boot, according to claim 4, where at least a portion of the distal end of the dual-end set-screw extends past the distal end of the set-screw bore, when engaged thereto, to form an external mounting screw portion.

6. The modular prosthetic force distribution boot, according to claim 5, wherein the external mounting screw portion can be removably attached to the strut receiver of the hydraulic dashpot.

7. The modular prosthetic force distribution boot, according to claim 6, wherein the strut receiver is:
    a femoral subperiosteal strut receiver comprising a receiver housing with an exterior surface and internal threading by which the femoral subperiosteal strut can be removably attached, and
    wherein the bladder can be fixedly attached to some portion of the exterior surface of the femoral subperiosteal strut receiver, such that the portion of the bladder extends distally from the femoral subperiosteal strut receiver.

8. The modular prosthetic force distribution boot, according to claim 2, further comprising:
    a diaphragm disposed within the sleeve that divides the interior space into a proximal femur socket, and distal set-screw bore, where the femur socket receives at least the residual bone end.

9. The modular prosthetic force distribution boot, according to claim 8, further comprising a modified set-screw that can engage with the set-screw bore.

10. The modular prosthetic force distribution boot, according to claim 2, wherein the distal end of the sleeve comprises threading that can be operably and removably engaged with the strut receiver.

11. The modular prosthetic force distribution boot, according to claim 9, where at least a portion of a distal end of the modified set-screw extends past a distal end of the set-screw bore, when engaged thereto, to form an external mounting screw portion.

12. The modular prosthetic force distribution boot, according to claim 11, wherein the external mounting screw portion can be removably attached to the strut receiver of the hydraulic dashpot.

13. The modular prosthetic force distribution boot, according to claim 12, wherein the hydraulic dashpot is an above-knee hydraulic dashpot, comprising:
   a femoral subperiosteal strut receiver having a receiver housing with an exterior surface and internal threading by which the femoral subperiosteal strut can be removably attached, and
   the bladder fixedly attached to some portion of the exterior surface of the femoral subperiosteal strut receiver, such that the portion of the bladder extends distally from the femoral subperiosteal strut receiver.

14. The modular prosthetic force distribution boot, according to claim 3, further comprising a collared set-screw having a proximal end that can be attached to an intermedullary space of the residual bone end and a distal end that engages with the set-screw port within the diaphragm.

15. The modular prosthetic force distribution boot, according to claim 14, wherein the distal end of the sleeve comprises threading that can be operably and removably engaged with the strut receiver.

16. The modular prosthetic force distribution boot, according to claim 15, wherein the hydraulic dashpot is an above-knee hydraulic dashpot, comprising:
   a femoral subperiosteal strut receiver having a receiver housing with an exterior surface and internal threading by which the femoral subperiosteal strut can be removably attached, and
   the bladder fixedly attached to some portion of the exterior surface of the femoral subperiosteal strut receiver, such that the portion of the bladder extends distally from the femoral subperiosteal strut receiver.

17. The modular prosthetic force distribution boot, according to claim 15, wherein an external mounting screw portion is removably screwed into the strut receiver.

18. The modular prosthetic force distribution boot, according to claim 10, wherein an external mounting screw portion is removably screwed into the strut receiver.

19. The modular prosthetic force distribution boot, according to claim 18, wherein the hydraulic dashpot is an above-knee hydraulic dashpot, comprising:
   a femoral subperiosteal strut receiver having a receiver housing with an exterior surface and internal threading by which the femoral subperiosteal strut can be removably attached, and
   the bladder fixedly attached to some portion of the exterior surface of the femoral subperiosteal strut receiver, such that the portion of the bladder extends distally from the femoral subperiosteal strut receiver.

20. The modular prosthetic force distribution boot, according to claim 10, wherein the distal end of the subperiosteal strut is removably screwed into a receiver housing.

21. The modular prosthetic force distribution boot, according to claim 2, wherein the strut receiver is:
   a femoral subperiosteal strut receiver comprising a receiver housing with an exterior surface and internal threading by which the femoral subperiosteal strut can be removably attached, and
   wherein the bladder can be fixedly attached to some portion of the exterior surface of the femoral subperiosteal strut receiver, such that the portion of the bladder extends distally from the femoral subperiosteal strut receiver.

22. The modular prosthetic force distribution boot, according to claim 2, further comprising one or more stanchions extending proximally from the subperiosteal strut.

23. The modular prosthetic force distribution boot, according to claim 22, wherein the stanchions are formed as part of the subperiosteal strut.

24. The modular prosthetic force distribution boot, according to claim 22, wherein the stanchions can be separately affixed to the subperiosteal strut.

25. The modular prosthetic force distribution boot, according to claim 1, wherein the subperiosteal strut is a tibial-fibial subperiosteal strut comprising:
   a tibial socket having an opening in the proximal end for receiving a first residual bone end, such that the residual bone end abuts the tibial socket;
   a fibial socket juxtaposed with the tibial socket and having an opening in a proximal end for receiving a second residual bone end, such that the second residual bone end abuts the fibial socket; and
   a support bridge that connects and maintains the juxtaposition of the tibial socket and the fibial socket.

26. The modular prosthetic force distribution boot, according to claim 25, wherein the hydraulic dashpot is a below-knee hydraulic dashpot, comprising:
   a dual-strut receiver having a first seat and a second seat by which the tibial-fibial subperiosteal strut can be removably attached, the dual-strut receiver further having an exterior surface; and
   a bladder fixedly attached to the exterior surface of the dual-strut receiver, such that the bladder extends distally from the dual-strut receiver.

27. The modular prosthetic force distribution boot, according to claim 25, wherein the tibial socket and/or fibial socket further comprises one or more socket flanges to which the support bridge is adjustably connected.

28. The modular prosthetic force distribution boot, according to claim 25, wherein the tibial socket and fibial socket comprise bands that surround at least the first and second residual bone ends.

29. The modular prosthetic force distribution boot, according to claim 25, wherein the tibial socket and the fibial socket comprise cup-like openings into which at least the first and second residual bone ends can be received.

30. The modular prosthetic force distribution boot, according to claim 25, further comprising one or more stanchions extending proximally from the subperiosteal strut.

31. The modular prosthetic force distribution boot, according to claim 30, wherein the stanchions are formed as part of the subperiosteal strut.

32. The modular prosthetic force distribution boot, according to claim 30, wherein the stanchions can be separately affixed to the subperiosteal strut.

33. The modular prosthetic force distribution boot, according to claim 1, wherein the bladder has minimal elasticity such that there is minimal shape distortion with the application of force.

34. The modular prosthetic force distribution boot, according to claim 1, wherein the bladder has an asymmetric thickness.

35. The modular prosthetic force distribution boot, according to claim 1, wherein the bladder is filled with a biocompatible substance that is liquid, semi-liquid, solid, semi-solid, gel, gas, or some combination thereof.

36. The modular prosthetic force distribution boot, according to claim 1, wherein the bladder comprises a solid, elastic material which is increasingly less elastic and more dense towards the strut receiver.

37. The modular prosthetic force distribution boot, according to claim 1, further comprising one or more stanchions extending proximally from the subperiosteal strut.

38. The modular prosthetic force distribution boot, according to claim 37, wherein the stanchions are formed as part of the subperiosteal strut.

39. The modular prosthetic force distribution boot, according to claim 37, wherein the stanchions can be separately affixed to the subperiosteal strut.

40. The modular prosthetic force distribution boot, according to claim 37, further comprising a plurality of screw holes within the subperiosteal strut, the strut receiver, and the stanchions.

41. The modular prosthetic force distribution boot, according to claim 40, further comprising a plurality of anchoring screws utilized with the screw holes.

42. The modular prosthetic force distribution boot, according to claim 37, wherein the stanchions are attached to the residual bone with an adhesive material.

43. The modular prosthetic force distribution boot, according to claim 37, further comprising one or more blades fixedly attached to the one or more stanchions.

44. The modular prosthetic force distribution boot, according to claim 43, wherein the blades are operably connected to an electromagnetic attachment system in a prosthetic limb.

45. The modular prosthetic force distribution boot, according to claim 44, wherein the blades are compatible with the electromagnetic attachment system.

46. The modular prosthetic force distribution boot, according to claim 45, wherein the electromagnetic attachment system is controlled by one or more sensors on-board the prosthetic limb.

47. The modular prosthetic force distribution boot, according to claim 46, wherein the sensors cause the operable connection between the blades and the electromagnetic attachment system to cycle between different strengths of attachment.

48. An electromagnetically operated prosthetic limb system comprising:
   an implantable modular force distribution boot comprising,
      a subperiosteal strut having a proximal end and a distal end, where the proximal end receives the residual bone end in an amputated limb, such that at least the residual bone end abuts the subperiosteal strut;
      at least one stanchion attached to and extending from the proximal end of the subperiosteal strut;
      a hydraulic dashpot comprising,
         a strut receiver to which the distal end of the subperiosteal strut can be removably attached; and
         a bladder fixedly attached to the strut receiver, and
      at least one blade fixedly attached to the at least one stanchion,
   an external prosthetic device comprising,
      at least one electromagnet positioned within the external prosthetic device such that it forms an operable connection with the at least one blade, and
      at least one sensor operably connected to the at least one electromagnet, wherein the at least one sensor detects the position of the prosthetic device, so as to cause the operable connection of the at least one electromagnet to the at least one blade, to be activated or inactivated depending upon the position of the prosthetic device,
   such that when the operable connection between the at least one blade and the at least one electromagnet is activated, the attractive forces between them maintain the position of the external prosthetic device against a residual limb, so that forces exerted on or about the terminal end of the amputated limb, from the residual bone end or the external prosthetic device, are absorbed and/or redistributed internally by the bladder.

49. The modular force distribution boot according to claim 48, wherein the subperiosteal strut is a femoral subperiosteal strut comprising a sleeve having a proximal end and a distal end and an interior space there between, for receiving at least the residual bone end.

50. The electromagnetically operated prosthetic limb system according to claim 49, further comprising:
   a diaphragm disposed within the sleeve that divides the interior space into a proximal femur socket and distal set-screw bore, where the femur socket receives at least the residual bone end, and
   a set-screw port within the diaphragm that communicates the femur socket with the set-screw bore.

51. The electromagnetically operated prosthetic limb system according to claim 50, further comprising a dual-end set-screw having a proximal end that can extend through the set-screw port into the femur socket and be attached to an intermedullary space of the residual bone and a distal end that engages with the set-screw bore.

52. The electromagnetically operated prosthetic limb system according to claim 51, wherein at least a portion of the distal end of the dual-end set-screw extends past the distal end of the set-screw bore when engaged thereto to form an external mounting screw portion.

53. The electromagnetically operated prosthetic limb system according to claim 52, wherein the external mounting screw portion can be removably attached to the strut receiver of the hydraulic dashpot.

54. The electromagnetically operated prosthetic limb system according to claim 53, wherein the strut receiver is a femoral subperiosteal strut receiver comprising a receiver housing with an exterior surface and internal threading by which the femoral subperiosteal strut can be removably attached;
   and wherein the bladder can be fixedly attached to some portion of the exterior surface of the femoral subperiosteal strut receiver, such that that a portion of the bladder extends distally from the femoral subperiosteal strut receiver.

55. The electromagnetically operated prosthetic limb system according to claim 50, further comprising a collared set-screw having a proximal end that can be attached to the intermedullary space of the residual bone end and a distal end that engages with the set-screw port within the diaphragm.

56. The electromagnetically operated prosthetic limb system according to claim 55, wherein the distal end of the sleeve comprises threading that can be operably and removably engaged with the strut receiver.

57. The electromagnetically operated prosthetic limb system according to claim 56, wherein the hydraulic dashpot is an above-knee hydraulic dashpot, comprising:
   a femoral strut receiver having a receiver housing with an exterior surface and internal threading by which the femoral subperiosteal strut can be removably attached; and
   the bladder fixedly attached to some portion of the exterior surface, such that a portion of the bladder extends distally from the femoral strut receiver.

58. The electromagnetically operated prosthetic limb system according to claim 56, wherein an external mounting screw portion is removably screwed into the strut receiver.

59. The electromagnetically operated prosthetic limb system according to claim 49, further comprising:
   a diaphragm disposed within the sleeve that divides the interior space into a proximal femur socket and distal set-screw bore, where the femur socket receives at least the residual bone end.

60. The electromagnetically operated prosthetic limb system according to claim 59, further comprising a modified set-screw that can engage with the set-screw bore.

61. The electromagnetically operated prosthetic limb system according to claim 60, wherein an external mounting screw portion is removably screwed into the strut receiver.

62. The electromagnetically operated prosthetic limb system according to claim 60, wherein at least a portion of a distal end of the modified set-screw extends past a distal end of the set-screw bore when engaged thereto to form an external mounting screw portion.

63. The electromagnetically operated prosthetic limb system according to claim 62, wherein the external mounting screw portion can be removably attached to the strut receiver of the hydraulic dashpot.

64. The electromagnetically operated prosthetic limb system according to claim 63, wherein the hydraulic dashpot is an above-knee hydraulic dashpot, comprising:
a femoral strut receiver having a receiver housing with an exterior surface and internal threading by which the femoral subperiosteal strut can be removably attached; and
the bladder fixedly attached to some portion of the exterior surface, such that a portion of the bladder extends distally from the femoral strut receiver.

65. The electromagnetically operated prosthetic limb system according to claim 49, wherein the distal end of the sleeve comprises threading that can be operably and removably engaged with the strut receiver.

66. The electromagnetically operated prosthetic limb system according to claim 65, wherein the hydraulic dashpot is an above-knee hydraulic dashpot, comprising:
a femoral strut receiver having a receiver housing with an exterior surface and internal threading by which the femoral subperiosteal strut can be removably attached; and
the bladder fixedly attached to some portion of the exterior surface, such that a portion of the bladder extends distally from the femoral strut receiver.

67. The electromagnetically operated prosthetic limb system according to claim 65, wherein the distal end of the subperiosteal strut is removably screwed into a receiver housing.

68. The electromagnetically operated prosthetic limb system according to claim 49, wherein the strut receiver is a femoral subperiosteal strut receiver comprising a receiver housing with an exterior surface and internal threading by which the femoral subperiosteal strut can be removably attached;
and wherein the bladder can be fixedly attached to some portion of the exterior surface of the femoral subperiosteal strut receiver, such that a portion of the bladder extends distally from the femoral subperiosteal strut receiver.

69. The electromagnetically operated prosthetic limb system according to claim 49, wherein the at least one stanchion extends proximally from the subperiosteal strut for attachment to the residual bone.

70. The electromagnetically operated prosthetic limb system according to claim 69, wherein the at least one stanchion is formed as part of the subperiosteal strut.

71. The electromagnetically operated prosthetic limb system according to claim 69, wherein the at least one stanchion is formed as part of the subperiosteal strut.

72. The electromagnetically operated prosthetic limb system according to claim 69, wherein the at least one stanchion is separately affixed to the subperiosteal strut.

73. The electromagnetically operated prosthetic limb system according to claim 48, wherein the subperiosteal strut is a tibial-fibial subperiosteal strut comprising:
a tibial socket having an opening in the proximal end for receiving at least a first residual bone end, such that the first residual bone end abuts the tibial socket;
a fibial socket juxtaposed with the tibial socket and having an opening in the proximal end for receiving at least a second residual bone end, such that the second residual bone end abuts the final socket; and
a support bridge that connects and maintains the juxtaposition of the tibial socket and the fibial socket.

74. The electromagnetically operated prosthetic limb system according to claim 73, wherein the tibial socket and/or fibial socket further comprises one or more socket flanges to which the support bridge is adjustably connected.

75. The electromagnetically operated prosthetic limb system according to claim 73, wherein the tibial socket and fibial socket comprise bands that surround the at least the first and second residual bone ends.

76. The electromagnetically operated prosthetic limb system according to claim 73, wherein the tibial socket and the final socket comprise cup-like openings into which residual bone ends can be seated.

77. The electromagnetically operated prosthetic limb system according to claim 73, wherein the hydraulic dashpot is a below-knee hydraulic dashpot, comprising:
a dual-strut receiver having a first seat and a second seat by which the tibial-fibial subperiosteal strut can be removably attached, the dual-strut receiver further having an exterior surface; and
the bladder fixedly attached to an exterior surface of the dual-strut receiver, such that the bladder extends distally from the dual-strut receiver.

78. The electromagnetically operated prosthetic limb system according to claim 73, wherein the at least one stanchion extends proximally from the subperiosteal strut for attachment to the residual bone end.

79. The electromagnetically operated prosthetic limb system according to claim 78, wherein the at least one stanchion is formed as part of the subperiosteal strut.

80. The electromagnetically operated prosthetic limb system according to claim 78, wherein the at least one stanchion is separately affixed to the subperiosteal strut.

81. The electromagnetically operated prosthetic limb system according to claim 48, wherein the at least one stanchion extends proximally from the subperiosteal strut for attachment to the residual bone.

82. The electromagnetically operated prosthetic limb system according to claim 81, further comprising a plurality of screw holes within the subperiosteal strut, the strut receiver, and the stanchions.

83. The electromagnetically operated prosthetic limb system according to claim 82, further comprising a plurality of anchoring screws utilized with the screw holes.

84. The electromagnetically operated prosthetic limb system according to claim 81, wherein the at least one stanchion is separately affixed to the subperiosteal strut.

85. The electromagnetically operated prosthetic limb system according to claim 81, wherein the stanchions are attached to the residual bone end with an adhesive material.

86. The electromagnetically operated prosthetic limb system according to claim 48, wherein the bladder has minimal elasticity such that there is minimal shape distortion with the application of force.

87. The electromagnetically operated prosthetic limb system according to claim 48, wherein the bladder has an asymmetric thickness.

88. The electromagnetically operated prosthetic limb system according to claim 48, wherein the bladder comprises a solid, elastic material which is increasingly less elastic and more dense towards the strut receiver.

* * * * *